US011667639B2

(12) United States Patent
Lisanti et al.

(10) Patent No.: US 11,667,639 B2
(45) Date of Patent: Jun. 6, 2023

(54) MITOKETOSCINS: MITOCHONDRIAL-BASED THERAPEUTICS TARGETING KETONE METABOLISM IN CANCER CELLS

(71) Applicant: LUNELLA BIOTECH, INC., Ottawa (CA)

(72) Inventors: Michael P. Lisanti, Fulton, MD (US); Federica Sotgia, Fulton, MD (US)

(73) Assignee: LUNELLA BIOTECH, INC., Ontario (CA)

( * ) Notice: Subject to any disclaimer, the term of this patent is extended or adjusted under 35 U.S.C. 154(b) by 80 days.

(21) Appl. No.: 16/626,426

(22) PCT Filed: Jun. 25, 2018

(86) PCT No.: PCT/US2018/039394
§ 371 (c)(1),
(2) Date: Dec. 24, 2019

(87) PCT Pub. No.: WO2019/005698
PCT Pub. Date: Feb. 3, 2019

(65) Prior Publication Data
US 2020/0148688 A1    May 14, 2020

Related U.S. Application Data

(60) Provisional application No. 62/524,829, filed on Jun. 26, 2017.

(51) Int. Cl.
| C07D 487/04 | (2006.01) |
| C07D 209/42 | (2006.01) |
| G16C 20/50  | (2019.01) |
| C07D 265/36 | (2006.01) |
| C07D 417/12 | (2006.01) |
| C40B 30/06  | (2006.01) |
| C40B 40/14  | (2006.01) |

(52) U.S. Cl.
CPC ......... *C07D 487/04* (2013.01); *C07D 209/42* (2013.01); *C07D 265/36* (2013.01); *C07D 417/12* (2013.01); *C40B 30/06* (2013.01); *C40B 40/14* (2013.01); *G16C 20/50* (2019.02)

(58) Field of Classification Search
CPC .................................................. C07D 487/04
See application file for complete search history.

(56) References Cited

U.S. PATENT DOCUMENTS

| 3,517,067 | A | 6/1970 | Stern |
| 5,168,057 | A | 12/1992 | Oh et al. |
| 5,250,518 | A | 10/1993 | Kobrehel et al. |
| 5,441,939 | A | 8/1995 | Yang |
| 5,795,871 | A | 8/1998 | Narita et al. |
| 6,043,226 | A | 3/2000 | Lundy et al. |
| 6,165,999 | A | 12/2000 | Vu |
| 6,475,518 | B1 | 11/2002 | Baumgart et al. |
| 6,858,598 | B1 | 2/2005 | McKearn et al. |
| 7,405,227 | B2 | 7/2008 | Kun et al. |
| 7,485,298 | B2 | 2/2009 | Powell |
| 8,075,902 | B2 | 12/2011 | Powell |
| 8,357,723 | B2 | 1/2013 | Satyam |
| 8,728,546 | B1* | 5/2014 | Peskin ................... A61P 35/00 424/725 |
| 8,741,853 | B2 | 6/2014 | Steliou |
| 9,394,233 | B2 | 7/2016 | Merino et al. |
| 9,675,578 | B2 | 6/2017 | Desai et al. |
| 9,801,922 | B2 | 10/2017 | Spitz et al. |
| 2005/0002942 | A1 | 1/2005 | Vlahov et al. |
| 2005/0256081 | A1 | 11/2005 | Peyman |
| 2007/0048296 | A1 | 3/2007 | Kajander et al. |
| 2007/0105937 | A1 | 5/2007 | Pappolla et al. |
| 2007/0292906 | A1 | 12/2007 | Cheng et al. |
| 2008/0045589 | A1 | 2/2008 | Kelley |
| 2008/0160007 | A1 | 7/2008 | Powell |
| 2008/0241959 | A1 | 10/2008 | Culic et al. |
| 2009/0311249 | A1 | 12/2009 | Gianni et al. |
| 2010/0120679 | A1 | 5/2010 | Xu et al. |
| 2010/0202969 | A1 | 8/2010 | Panyam et al. |
| 2010/0285001 | A1 | 11/2010 | Land et al. |
| 2012/0071465 | A1 | 3/2012 | Clement et al. |
| 2012/0141467 | A1 | 6/2012 | Schneider |

(Continued)

FOREIGN PATENT DOCUMENTS

| EP | 0656422 | 6/1995 |
| EP | 0941998 | 9/2004 |

(Continued)

OTHER PUBLICATIONS

Sulpis et al. ("Calcium carbonate dissolution patterns in the ocean," Nature Geoscience, 2021, 14, 423-428, abstract).*
International Search Report and Written Opinion of the ISA for PCT/US2018/039354, dated Oct. 25, 2018, 12 pages.
International Preliminary Report on Patentability with Amended Sheets for PCT/US2018/039354, dated Aug. 219, 2019, 17 pages.
Anonymous, "Compound Summary for CID 6736 ", PUBCHEM Compound, Mar. 26, 2005, https://pubchem.ncbi.nlm.nih.gov/compound/6736 , Retrieved from the internet, pp. 1-60.
Ozsvari et al., "Mitoketoscins: Novel mitochondrial inhibitors for targeting ketone metabolism in cancer stem cells (CSCs)", Sep. 24, 2017, Oncotarget: vol. 8, No. 45, pp. 78340-78350.

(Continued)

*Primary Examiner* — Yong S. Chong
(74) *Attorney, Agent, or Firm* — Nixon & Vanderhye, P.C.

(57) ABSTRACT

The present disclosure relates to compounds that bind to at least one of ACAT1/2 and OXCT1/2 and inhibit mitochondrial ATP production, referred to herein as mitoketoscins. Methods of screening compounds for mitochondrial inhibition and anti-cancer properties are disclosed. Also described are methods of using mitoketoscins to prevent or treat cancer, bacterial infections, and pathogenic yeast, as well as methods of using mitoketoscins to provide anti-aging benefits. Specific mitoketoscin compounds are also disclosed.

7 Claims, 17 Drawing Sheets

(56) References Cited

U.S. PATENT DOCUMENTS

| | | |
|---|---|---|
| 2013/0040327 A1 | 2/2013 | Chang et al. |
| 2013/0172430 A1 | 7/2013 | Lisanti et al. |
| 2014/0142056 A1 | 5/2014 | Shanmugam et al. |
| 2014/0187611 A1 | 7/2014 | Auwerx et al. |
| 2014/0303085 A1 | 10/2014 | Wong et al. |
| 2014/0364595 A1 | 12/2014 | Bapat et al. |
| 2015/0079154 A1 | 3/2015 | Zender et al. |
| 2015/0224169 A1 | 8/2015 | Bhatia et al. |
| 2015/0224206 A1 | 8/2015 | Van |
| 2015/0231069 A1 | 8/2015 | Modi |
| 2016/0008332 A1 | 1/2016 | Haq et al. |
| 2016/0339106 A1 | 11/2016 | Shanta |
| 2017/0035832 A1 | 2/2017 | Liu et al. |
| 2017/0095460 A1 | 4/2017 | Fathi et al. |
| 2017/0224730 A1 | 8/2017 | Berenson |
| 2017/0232008 A1 | 8/2017 | Zeicher |
| 2018/0214472 A1 | 8/2018 | Bapat et al. |

FOREIGN PATENT DOCUMENTS

| | | |
|---|---|---|
| JP | 2016-155679 | 9/2016 |
| RU | 2346942 C2 | 7/2004 |
| SU | 2074179 C1 | 3/1992 |
| WO | 1995015770 | 6/1995 |
| WO | 99/26582 | 6/1999 |
| WO | 2010/121177 | 10/2010 |
| WO | WO 2012024612 | 2/2012 |
| WO | 2013/040206 | 3/2013 |
| WO | 2015/191668 | 12/2015 |
| WO | 2016/027089 | 2/2016 |
| WO | 2016/059247 | 4/2016 |
| WO | 2018/027252 | 2/2018 |
| WO | 2018/136598 | 7/2018 |
| WO | 2018/136617 | 7/2018 |
| WO | 2018/195434 | 10/2018 |
| WO | 2018/195446 | 10/2018 |
| WO | 2018/202910 | 11/2018 |
| WO | 2018/213751 | 11/2018 |
| WO | 2018/213764 | 11/2018 |
| WO | 2018/218242 | 11/2018 |

OTHER PUBLICATIONS

Lamb, et al., "Antibiotics that target mitochondria effectively eradicate cancer stem cells, across multiple tumor types: Treating cancer like an infectious disease", Oncotarget, Jan. 22, 2015, vol. 6, No. 7, pp. 4569-4584.
Giacometti et al., "In-vitro activity of macrolides alone and in combination with artemisin, atovaquone, dapsone, minocycline or pyrimethamine against *Cryptosporidium parvum*". Journal of Antimicrobial Chemotherapy, 1996, vol. 38, pp. 399-408.
M2 Pharma [London], "Study finds vitamin C and antibiotics effectively killed cancer stem cells", Jun. 13, 2017, 2 pages.
Sotgia et al., "A mitochondrial based oncology platform for targeting cancer stem cells (CSCs): MITO-ONC-RX", Journal Cell Cycle, Sep. 26, 2018, vol. 17, No. 17, pp. 2091-2100.
Komatsu et al., "Clarithromycin enhances bortezomib-induced cytotoxicity via endoplasmic reticulum stress-mediated CHOP (GADD153) induction and autophagy in breast cancer cells", International Journal of Oncology, vol. 40, 2012, pp. 1029-1039.
Moriya et al., "Macrolide antibiotics block autophagy flux and sensitize to bortezomib via endoplasmic reticulum stress-mediated CHOP induction in myeloma cells", International Journal of Oncology, vol. 42, 2013, pp. 1541-1550.
Petovari et al., "Targeting cellular metabolism using rapamycin and/or doxycycline enhances anti-tumour effects in human glioma cells", Cancer Cell Int., 18:211, 2018, pp. 1-17.
Van Nuffel et al., "Repurposing Drugs in Oncology (ReDO)—clarithromycin as an anti-cancer agent", ecancermedicalscience, 2015, pp. 1-26.
Jankowitsch et al., "A novel N,N-8-amino-8-demethyl-D-riboflavin dimethyltransferase (RosA) catalyzing the two terminal steps of roseoflavin biosynthesis in *Streptomyces davawensis*", The American Society for Biochemistry and Molecular Biology, Inc., 2011, pp. 1-25.
Murphy, "Targeting lipophilic cations to mitochondria", Biochimica et Biophysica Acta, 2008, pp. 1028-1031.
Ross et al., "Lipophilic Triphenylphosphonium Cations as Tools in Mitochondrial Bioenergetics and Free Radical Biology", Biochemistry (Moscow), vol. 70, No. 2, 2005, pp. 222-230. [Translated from Biokhimiya].
Gonzalez et al., "Mitochondria, Energy and Cancer: The Relationship with Ascorbic Acid", JOM, vol. 25, No. 1, 2010, pp. 29-38.
Examination Report in Australian Application No. 2018292283, dated Apr. 17, 2020.
CAS Reg No. 1047387-08-5, 1H-Indole-3-propanamide, 1-methyl-N-[2-(1-piperidinyl)ethyl]-β-[3-(trifluoromethyl)phenyl]—.
CAS Reg No. 1022389-70-3, 1H-Indole-3-propanamide, 1-methyl-β-(3-methylphenyl)-N-[2-(1-piperidinyl)ethyl]—.
CAS Reg No. 1047743-48-5, 1H-Indole-3-propanamide, 5-nitro-N-[2-(1-pyrrolidinyl)ethyl]-β-[3-(trifluoromethyl)phenyl]—.
Hughes, J. P. et al. "Principles of early drug discovery" (Review), British Journal of Pharmacology, 2011, 162, 1239-1249.
Office Action for Chile Application No. 2019-3708 dated Apr. 7, 2021.
Subramaniam, S. et al. (2008) Virtual high throughput screening (vHTS)—A Perspective. Bioinformation 3:14-17.
Pubchem CID 3307632 Creado el Jul. 9, 2005. Acceso en: https://pubchem.ncbi.nlm.nih.gov/compound/3307632.
Garcia-Bermudez, Javier et al.: "Drugging ACAT1 for Cancer Therapy", Molecular Cell, 2016, 64(5), pp. 856-857 doi:10.1016/j.molcel.2016.11.023 (the entire document).
Qiao LS, et al. "Identification of potential ACAT-2 selective inhibitors using pharmacophore, SVM and SVR from Chinese herbs". Molecular diversity. Nov. 2016; 20(4):933-44.
Chhabria MT, et al. "Discovery of Novel Acyl Coenzyme A: Cholesterol Acyltransferase Inhibitors: Pharmacophore-Based Virtual Screening, Synthesis and Pharmacology". Chemical biology & drug design. Jul. 2012;80(1):106-13.
Hu H, et al. "First identification of xanthone sulfonamides as potent acyl-CoA: cholesterol acyltransferase (ACAT) inhibitors". Bioorganic & medicinal chemistry letters. May 15, 2010;20(10):3094-7.
Fraser ME, et al. "Catalytic role of the conformational change in succinyl-CoA: 3-oxoacid CoA transferase on binding CoA". Biochemistry. Dec. 7, 2010; 49(48):10319-28.
Trushina E, et al. "Tricyclic pyrone compounds prevent aggregation and reverse cellular phenotypes caused by expression of mutant huntingtin protein in striatal neurons". BMC neuroscience. Dec. 2009; 10(1):1-4.
Sotgia F, et al. "Mitochondria fuel breast cancer metabolism: fifteen markers of mitochondrial biogenesis label epithelial cancer cells, but are excluded from adjacent stromal cells". Cell cycle.
Ohta et al., "Novel 5-Hydroxytryptamine (5-HT$_3$) Receptor Antagonists. II.[1]) Synthesis and Structure-Activity Relationships of 4,5,6,7-Tetraphydro-1H-benzimidazole Derivatives", Chem. Pharm. Bull. vol. 44, No. 5, pp. 1000-1008, May 1996.
Orlandi et al., "Metal-Free Reduction of Aromatic and Aliphatic Nitro Compounds to Amines: A HSiCl$_3$-Mediated Reaction of Wide General Applicability", Org. Lett. 2015, 17, pp. 3941-3943.

* cited by examiner

Drug Screening & Validation

Virtual high-throughput screening (vHTS)

Step 1. Selection of two molecular libraries of 1000 compounds each (both for OXCT1 and ACAT1) from a small molecular screening collection of 30,000 compounds Step 2. Further analysis of predicted binding affinity and visual inspection Compounds performing well in all analysis steps were selected for assay

Phenotypic drug screening

ATP-depletion assays
on human breast cancer cells (MCF7)
84 Compounds (OXCT1); 143 compounds (ACAT1)
Observed 8 hits at 20 µM

Functional validation

Mammosphere assays
Metabolic Flux analysis
OCR/ECAR

Mitoketoscins

FIG. 1

Mitoketoscins
Compound 1
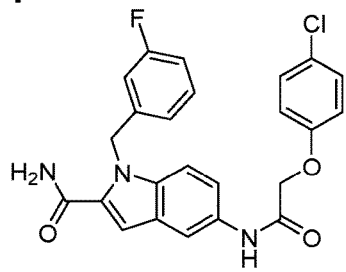
Compound 5
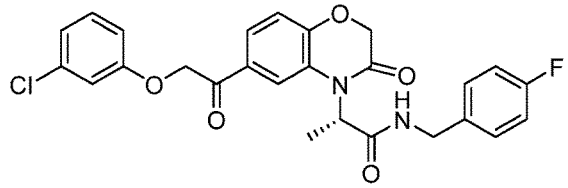
Compound 2
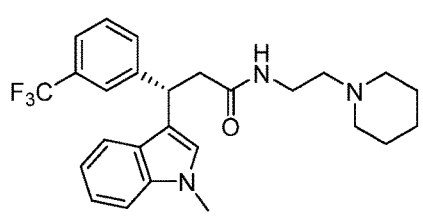
Compound 6
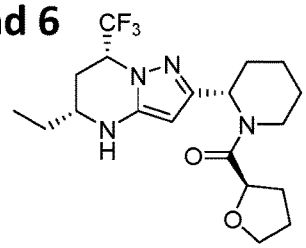
Compound 3
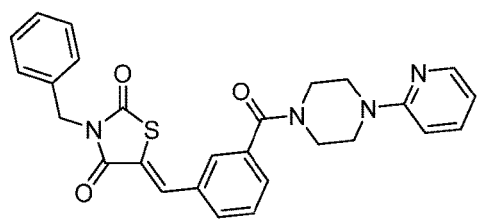
Compound 7
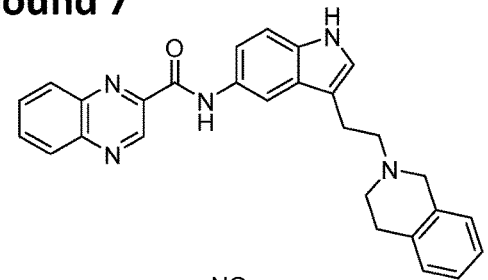
Compound 4
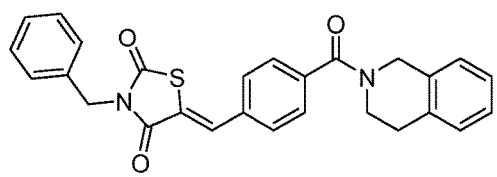
Compound 8
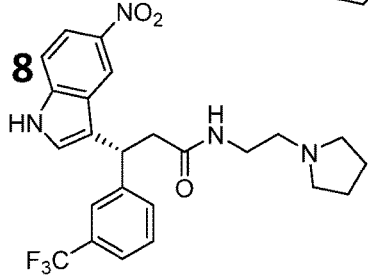
FIG. 2

3D-Spheroid CSC Assay (Mammospheres)

Compound 2

Compound 8

Compound 3

Compound 6

Summary of the Mitoketoscins
Compound 8
10.1 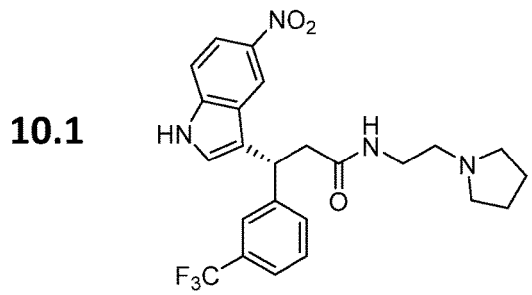
Compound 2
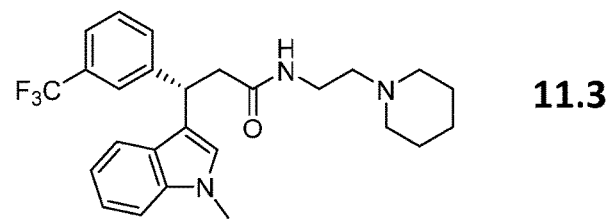 11.3
Compound 6
22.9 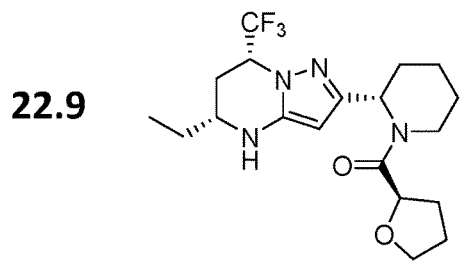
Compound 3
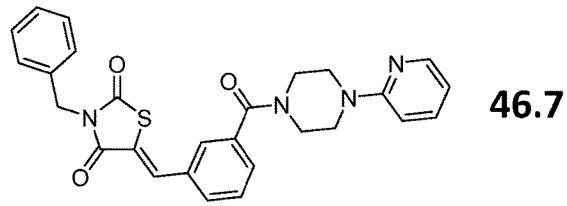 46.7
FIG. 10A
Arecoline
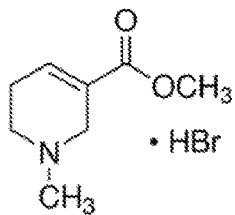
FIG. 10B

Pharmacophore: for Compounds 2 & 8

Mitoketoscins

MITOKETOSCINS: MITOCHONDRIAL-BASED THERAPEUTICS TARGETING KETONE METABOLISM IN CANCER CELLS

This application is the U.S. national phase of International Application No. PCT/US2018/039354 filed 25 Jun. 2018, which designated the U.S. and claims the benefit of U.S. application Ser. No. 62/524,829 filed 26 Jun. 2017, the entire contents of each of which are hereby incorporated by reference.

FIELD

The present disclosure relates to mitoketoscins-non-carcinogenic compounds that bind to at least one of ACAT1/2 and OXCT1/2 and inhibit mitochondrial ATP production, as well as methods for identifying mitoketoscins, methods of using the inhibitors to target cancer stem cells, to target bacteria and pathogenic yeast, and to provide anti-aging benefits, and pharmaceutical compositions for treating cancer, bacterial infections, yeast infections, and aging, containing one or more mitoketoscins as the active ingredient.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Ketones (3-hydroxybutyrate, acetoacetate and acetone) are high-energy mitochondrial fuels; they are naturally generated by hepatocytes during periods of caloric restriction, fasting, and/or starvation. During nutrient deprivation, ketone bodies secreted into the blood are then directed towards the brain, where neurons convert them back into Acetyl-CoA so they may be effectively re-utilized as an energy source. The two most critical neuronal enzymes for this ketone re-utilization process are OXCT1/2 and ACAT1/2, as they are directly involved in the conversion of ketone bodies into Acetyl-CoA. Martinez-Outschoorn et al., *Nat Rev Clin Oncol* 2017; 14(1):11-31.

The inventors showed that a similar "ketone-shuttle" also exists in human tumors, whereby ketogenic cancer-associated fibroblasts (CAFs) locally produce ketone bodies for re-utilization by mitochondria in adjacent human breast cancer cells. Martinez-Outschoorn, et al., *Cell Cycle* 2012; 11(21):3956-63. In further support of this "metabolic-coupling" hypothesis, the inventors found that recombinant over-expression of ACAT1/2 or OXCT1/2 in MDA-MB-231 breast cancer cells was indeed sufficient to promote tumor growth and lung metastasis. These data provide genetic evidence that ketone body re-utilization may help drive tumor progression and metastasis.

SUMMARY

In view of the foregoing background, it appears that the enzymes ACAT1/2 and OXCT1/2 may be bona-fide metabolic oncogenes. It is therefore an object of this disclosure to demonstrate that ketone re-utilization plays a critical role in the propagation and maintenance of many cancers. It is also an object of this disclosure to present methods for identifying mitoketoscins, non-carcinogenic compounds that bind to at least one of ACAT1/2 and OXCT1/2 and inhibit mitochondrial ATP production. It is also an object of this disclosure to identify mitoketoscins having anti-cancer and antibiotic properties. It is also an object of this disclosure to identify mitoketoscins having anti-aging properties. It is also an object of this disclosure to mitoketoscins that function as radiosensitizers and photosensitizers. The term "mitoketoscin" broadly refers to non-carcinogenic compounds that bind to at least one of ACAT1/2 and OXCT1/2 and inhibit mitochondrial ATP production. These compounds therefore are designed to target the mitochondrial enzymes responsible for ketone re-utilization and that have anti-cancer and antibiotic properties. These compounds bind to either or both active catalytic sites of OXCT1/2 and ACAT1/2 to inhibit mitochondrial function. The present disclosure further relates to methods of identifying mitoketoscins, methods of making such mitoketoscins, and methods of using mitoketoscins for therapeutic purposes.

Given their mitochondrial inhibition properties, mitoketoscins may similarly be used to target bacteria and pathogenic yeast, provide anti-aging benefits, function as radio-sensitizers and/or photo-sensitizers, sensitize bulk cancer cells and cancer stem cells to chemotherapeutic agents, pharmaceuticals, and/or other natural substances.

Mitoketoscins may be identified through a convergent approach of virtual high-throughput in silico screening followed by in vitro validation for mitochondrial inhibition. Mitoketoscins may be rapidly developed by combining in silico drug design with phenotypic drug screening.

BRIEF DESCRIPTION OF THE DRAWINGS

FIG. 1 shows a schematic diagram outlining a drug discovery strategy according to embodiments of the present approach.

FIG. 2 illustrates the chemical structures of eight candidate mitoketoscin compounds 1-8 identified following phenotypic drug screening.

FIG. 10A shows four candidate mitoketoscin compounds and their respective IC-50s for inhibiting CSC propagation. FIG. 10B shows the chemical structure of arecoline, a naturally occurring ACAT1 inhibitor.

DESCRIPTION

Figure 3A:
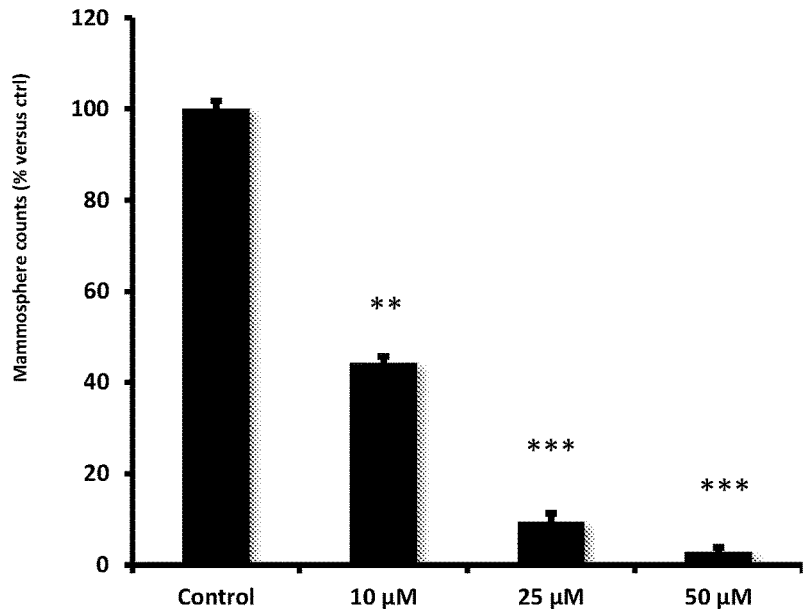
FIGS. 3A-F shows the effects of six candidate mitoketoscin compounds on mammosphere formation in MCF7 cells.
Figure 3B:
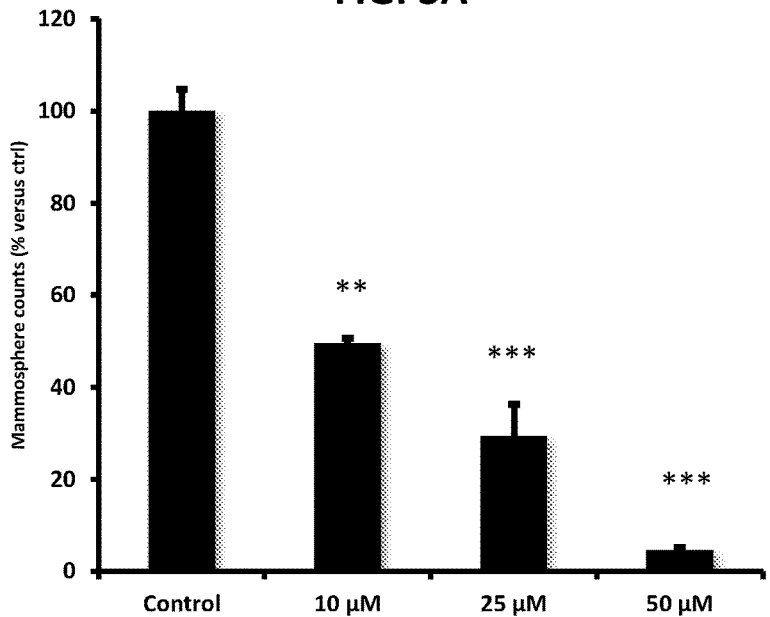
Figure 3C:
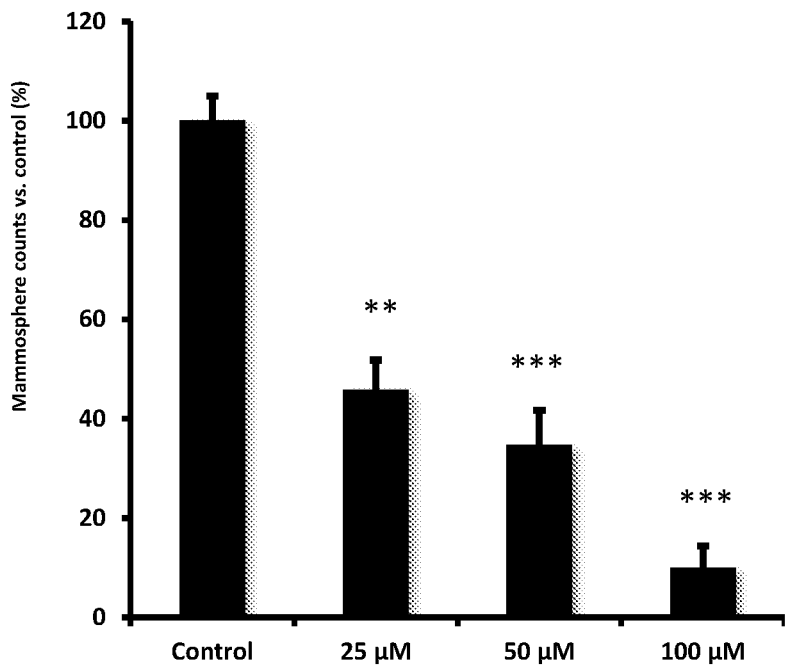
Figure 3D:
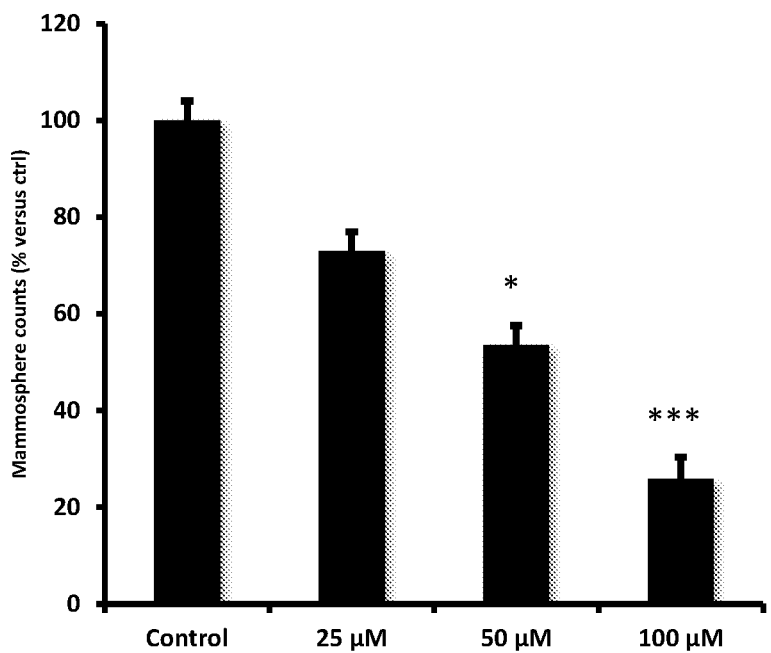
Figure 3E:
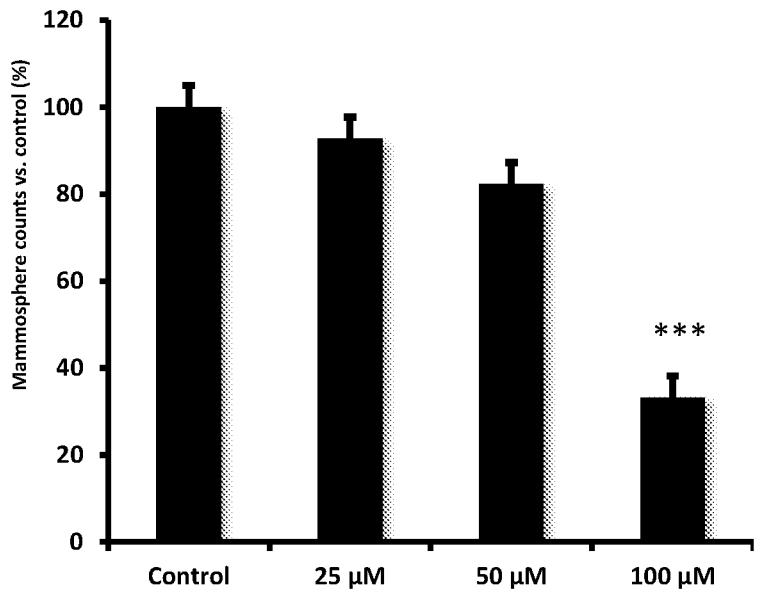
Figure 3F:
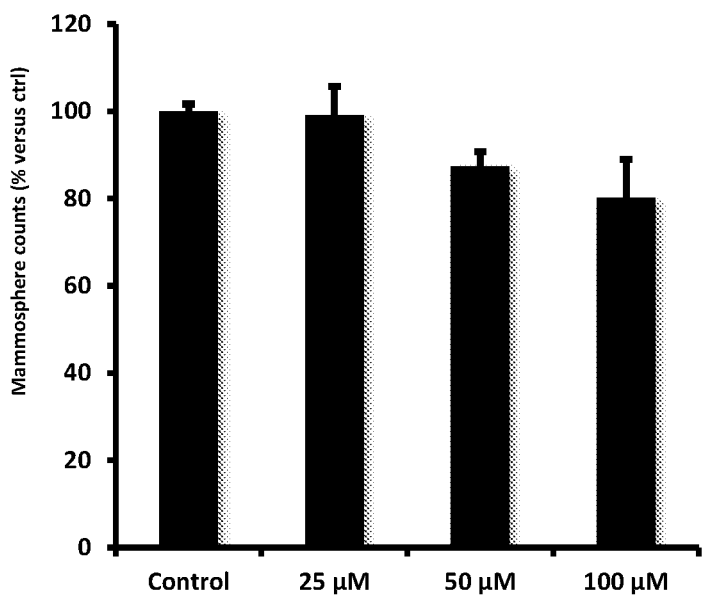

The following description illustrates embodiments of the present approach in sufficient detail to enable practice of the present approach. Although the present approach is described with reference to these specific embodiments, it should be appreciated that the present approach may be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

Mitochondrial metabolism is an untapped gateway for treating a number of afflictions, ranging from cancer to bacterial and fungal infections to aging. Functional mitochondria are required for the propagation of cancer stem cells. Inhibiting mitochondrial metabolism in cancer cells impedes the propagation of those cells. Mitochondrial inhibitors targeting the re-utilization of ketone bodies as mitochondrial fuels therefore represent a new class of anti-cancer therapeutics. These compounds may also inhibit mitochondrial protein translation, and therefore may function as broad-spectrum antibiotics that target both bacteria and pathogenic yeast. Research has also shown that mitochondrial inhibitors have anti-aging properties; hence mitoketoscins may also impart anti-aging benefits.

Novel inhibitors of mitochondrial ATP production that bind to at least one of OXCT1/2 and ACAT1/2—mitoketoscins—may be identified through a convergent approach of virtual high-throughput screening followed by in vivo validation for mitochondrial inhibition. FIG. 1 is an overview of methods for identifying mitoketoscins by using in silico drug screening and phenotypic drug screening disclosed herein. All or a portion of the three-dimensional structure of the porcine OXCT1 and human ACAT1 proteins may be used in step S101 to identify novel compounds that bind to these proteins through virtual high-throughput screening (vHTS) (i.e., in silico drug screening). The screening may be performed across a library of molecules. For instance, during initial investigations the inventors screened a collection of 30,000 small molecule compounds for compounds expected to bind anywhere to the succinyl-CoA: 3-ketoacid CoA transferase from pig heart covalently bound to CoA (PDB code 3OXO) or to the CoA binding site of human mitochondrial acetoacetyl-CoA thiolase (PDB code 2F2S). Initial vHTS may use various screening programs, such as the eHiTS screening program, to identify a subset of compounds having a strong binding affinity to either protein. For example, the inventors used eHiTS to identify the top 1,000 ranked compounds from an initial library, based on predicted binding affinity. eHiTS is a screening method that systematically covers the part of the conformational and positional search space that avoids severe steric clashes, producing highly accurate docking poses at a speed that is well-suited for virtual high-throughput screening.

It should be appreciated that those skilled in the art may select or develop methods for identifying a subset of compounds having a desired binding affinity. To efficiently perform the docking, a series of clip files may be prepared corresponding to the entire protein structure and each compound docked sequentially at each of the clip files. Consensus scoring of the top compounds may be carried out using AutoDock 4.2, based on the same general binding site for each compound predicted from the eHiTS screen. Further analysis of predicted binding affinity and visual inspection may be carried out using a number of methods, including for example a de novo design program such as SPROUT. See Law et al., *J Mol Struct*. 666: 651-657 (2003), which is incorporated by reference in its entirety, for information about SPROUT. Depending on the initial library size and results, a number of compounds may be selected for phenotypic drug screening. For example, the inventors selected 227 compounds that performed well in these analysis steps for phenotypic drug screening at step S103. 84 compounds were selected for the OXCT1-based phenotypic screen and 143 compounds were selected for the ACAT1-based phenotypic screen.

Phenotypic drug screening S103 may be accomplished by testing the mitochondrial inhibition of selected compounds in a selected cell line. For example, ATP depletion assays may be used. The inventors tested the selected 227 compounds on their ability to functionally induce ATP-depletion in MCF7 human breast cancer cells. Approximately 85% of cellular ATP is normally generated by OXPHOS in mitochondria, so ATP-depletion is a surrogate marker for mitochondrial inhibition. It should be appreciated that those skilled in the art may employ other surrogates for mitochondrial inhibition. However, for the ATP-depletion assay inventors employed, MCF7 cells (6,000 cells/well) were plated into black clear-bottom 96-well plates and incubated overnight before treatment. The 227 compounds identified by vHTS were applied to the plated MCF7 cells at a concentration of 20 µM and were screened for ATP depletion. Compounds showing ATP-depletion effects were subsequently re-screened at a lower concentration (10 µM) to identify the top eight compounds that most potently induce ATP-depletion. Compounds were tested after 72 hours of incubation and experiments were performed in duplicate. After treatment, media was aspirated from the wells and plates were washed with warm phosphate-buffered saline (PBS) supplemented with $Ca^{2+}$ and $Mg^{2+}$. Then, cells were incubated with a Hoechst 33342 (Sigma) staining solution (10 µg/ml) for 30 min and washed with PBS to estimate cell viability. Fluorescence was read with a plate reader using excitation/emission wavelengths at 355/460-nm. Then, a CellTiter-Glo luminescent assay (Promega) was performed to measure metabolic activity (ATP content) in the very same wells that were treated with a given compound. Assays were performed according to the manufacturer's protocol. Fluorescence intensity (Hoechst staining) and luminescence intensity (ATP content) were normalized to vehicle-alone treated controls and were displayed as percent control for comparison. All eight test compounds significantly depleted ATP levels in viable cells. It should be appreciated that those of skill in the art may choose to employ the same or similar ATP-depletion assays, modify such assays, or may replace the ATP-depletion assay with another methodology for screening selected compounds for mitochondrial inhibition (e.g., oxygen consumption assays).

The present approach includes methods of confirming cell viability. Persons of skill in the art may select one or more methods for confirming cell viability suitable for the particular embodiment. The inventors initially used the Sulphorhodamine (SRB) assay, which is based on the measurement of cellular protein content. After treatment for 72 hours in 96-well plates, cells were fixed with 10% trichloroacetic acid (TCA) for 1 hour in the cold room, and were dried overnight at room temperature. Then, cells were incubated with SRB for 15 min, washed twice with 1% acetic acid, and air dried for at least 1 hour. Finally, the protein-bound dye was dissolved in a 10 mM Tris, pH 8.8 solution and read using the plate reader at 540-nm. Using the SRB assay, the inventors selected only the compounds depleting ATP levels without prominent cytotoxicity for further analysis. Prominent cytotoxicity was defined as fewer than 30% of cells still on the plate. Of course, embodiments employing other cell viability confirmation methodology may select compounds for further analysis based on other considerations as may be known in the art.

The present approach further involves methods of functional validation at step S105, during which a compound's function as a mitochondrial inhibitor may be confirmed. A number of methods may be used for functional validation, including, for example, metabolic flux analysis, mammosphere assays, viability assays, and antibiotic (anti-bacterial and/or anti-fungal) activity. For example, the inventors determined extracellular acidification rates (ECAR) and real-time oxygen consumption rates (OCR) for MCF7 cells using the Seahorse Extracellular Flux (XF96) analyzer (Seahorse Bioscience, MA, USA). MCF7 cells were maintained in DMEM supplemented with 10% FBS (fetal bovine serum), 2 mM GlutaMAX, and 1% Pen-Strep. 5,000 cells per well were seeded into XF96-well cell culture plates, and incubated overnight at 37° C. in a 5% $CO_2$ humidified atmosphere. After 24 hours, cells were treated with selected compounds showing ATP-depletion without prominent cytotoxicity at various concentrations (or vehicle alone). After 72 hours of treatment, cells were washed in pre-warmed XF assay media (for OCR measurement, XF assay media was supplemented with 10 mM glucose, 1 mM Pyruvate, 2 mM L-glutamine and adjusted at pH 7.4). Cells were maintained in 175 μL/well of XF assay media at 37° C. in a non-$CO_2$ incubator for 1 hour. During incubation, 25 μL of 80 mM glucose, 9 μM oligomycin, 1M 2-deoxyglucose (for ECAR measurement) and 25 μL of 10 μM oligomycin, 9 μM FCCP, 10 μM rotenone, 10 μM antimycin A (for OCR measurement) in XF assay media was loaded into the injection ports of the XFe-96 sensor cartridge. During the experiment, the instrument injected these inhibitors into the wells at a given time point, while ECAR/OCR was measured continuously. ECAR and OCR measurements were normalized by protein content (using the Sulphorhodamine B assay). Data sets were analyzed by XFe-96 software, using one-way ANOVA and Student's t-test calculations. All experiments were performed in triplicate, and results validated the mitochondrial inhibition effects of the mitoketoscin compounds described herein. It should be appreciated that numerous methods are known for functional validation, and that persons of skill in the art may select one or more depending on the validation needs (e.g., other assays that measure or approximate mitochondrial function).

In summary, the present approach may include methods of identifying potential mitoketoscins using in silico drug screening and phenotypic drug screening. Novel compounds identified using this methodology may be tested for anti-cancer activity (e.g., the ability to inhibit mammosphere formation and cell migration) and may be further tested on distinct bacterial and/or yeast strains to investigate antimicrobial activity. FIG. 1 summarizes the general methods for drug screening and validation according to an embodiment of the present approach, but it should be appreciated that those of skill in the art may deviate from the specific examples disclosed herein without departing from the present approach.

The present approach has led to the identification of mitoketoscins that have anti-cancer properties, and embodiments of the present approach may take the form of one or more of these compounds, as well as pharmaceutical compositions including effective amounts of one or more of these compounds, and various methods of treatment using one or more of these compounds. Based on the inventors' initial screening and validation, the compounds identified in FIG. 2 have anti-cancer properties and are therefore mitoketoscins. In view of the inventors' research, these mitoketoscins are therefore candidates for clinical trial. It should be appreciated that the mitoketoscins identified in FIG. 2 are not exhaustive, but are merely those compounds that have been identified thus far using the novel methodology set forth herein. It should be appreciated by those skilled in the art that the therapeutically-effective amount of each compound, for a particular therapy can be determined through the application of straightforward procedures as are known in the art.

Some embodiments may take the form of one or more mitoketoscins. The embodiment may be included in a pharmaceutical composition for treating cancer, bacterial infection, and/or pathogenic yeast infection. For example, a mitoketoscin may be a general pharmacophore having the following structure (or a salt thereof):

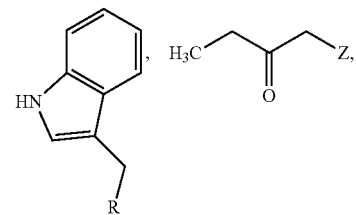

wherein Z is defined as ethylpiperidine or ethylpyrrolidine,

As another example, a mitoketoscin may be a general pharmacophore having the following structure (or a salt thereof):

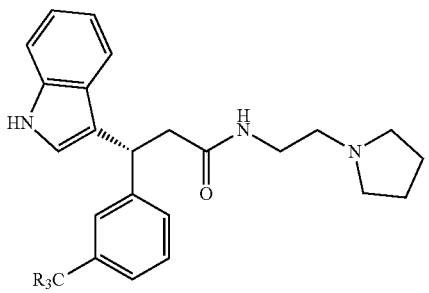

wherein each R may be the same or different and is selected from the group consisting of hydrogen, carbon, nitrogen, sulfur, oxygen, flourine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

As another example, a mitoketoscin may be a general pharmacophore having the following structure (or a salt thereof):

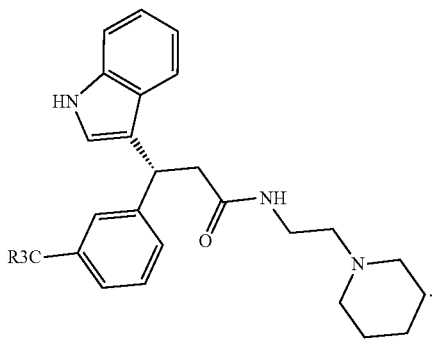

As a further example, a mitoketoscin may be a general pharmacophore having the following structure (or a salt thereof):

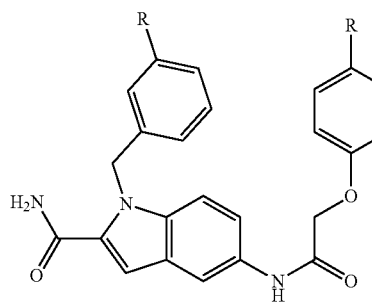

wherein each R may be the same or different and is selected from the group consisting of hydrogen, carbon, nitrogen, sulfur, oxygen, flourine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

As another example, a mitoketoscin may be a general pharmacophore having the following structure (or a salt thereof):

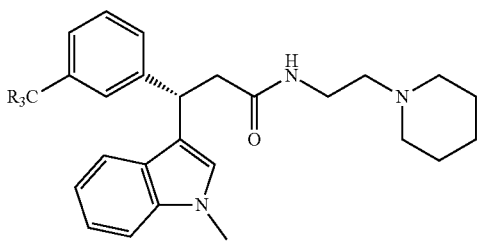

wherein each R may be the same or different and is selected from the group consisting of hydrogen, carbon, nitrogen, sulfur, oxygen, flourine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

Another example of a mitoketoscin is a general pharmacophore having the following structure (or a salt thereof):

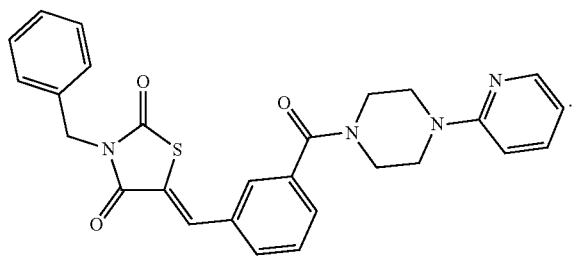 [SMILES: O=C(c1cccc(/C=C2\SC(=O)N(Cc3ccccc3)C2=O)c1)N1CCN(c2ccccn2)CC1]

A further example of a mitoketoscin is a general pharmacophore having the following structure (or a salt thereof):

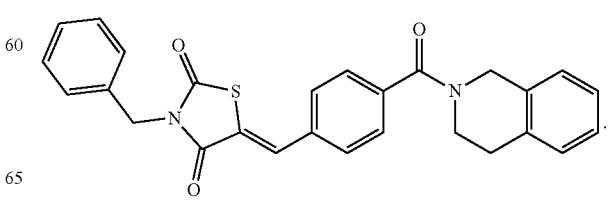

An additional example of a mitoketoscin is a general pharmacophore having the following structure (or a salt thereof):

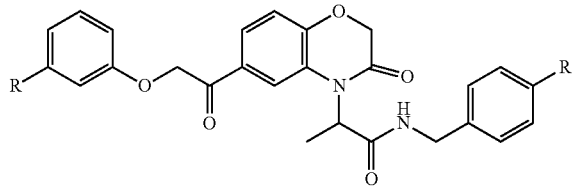

wherein each R may be the same or different and is selected from the group consisting of hydrogen, carbon, nitrogen, sulfur, oxygen, flourine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

Another example of a mitoketoscin is a general pharmacophore having the following structure (or a salt thereof):

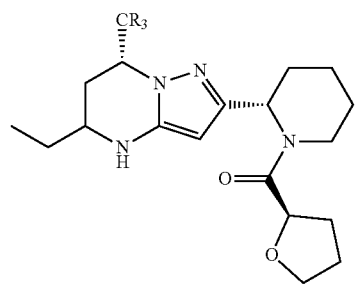

wherein each R may be the same or different and is selected from the group consisting of hydrogen, carbon, nitrogen, sulfur, oxygen, flourine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

A further example of a mitoketoscin is a general pharmacophore having the following structure (or a salt thereof):

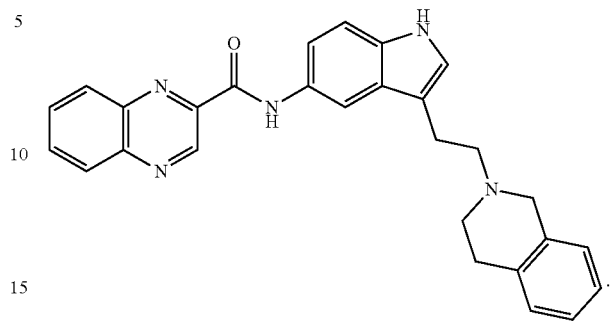

Another example of a mitoketoscin is a general pharmacophore having the following structure (or a salt thereof):

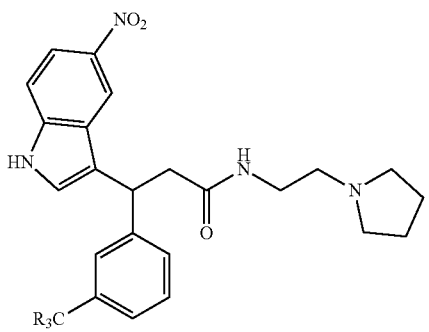

wherein each R may be the same or different and is selected from the group consisting of hydrogen, carbon, nitrogen, sulfur, oxygen, flourine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives. It should be appreciated that the mitoketoscins may be selected for therapeutic use individually, or in combination with more than one specific mitoketoscin, and/or with other substances to enhance the efficacy of other therapeutics. The therapeutics may be used in the form of usual pharmaceutical compositions which may be prepared using one or more known methods. For example, a pharmaceutical composition may be prepared by using diluents or excipients such as, for example, one or more fillers, bulking agents, binders, wetting agents, disintegrating agents, surface active agents, lubricants, and the like as are known in the art. Various types of administration unit forms may be selected depending on the therapeutic purpose(s). Examples of forms for pharmaceutical compositions include, but are not limited to, tablets, pills, powders, liquids, suspensions, emulsions, granules, capsules, suppositories, injection preparations (solutions and suspensions), topical creams, and other forms as may be known in the art. For the purpose of shaping a pharmaceutical composition in the form of tablets, any excipients which are known may be used, for example carriers such as lactose, white sugar, sodium chloride, glucose, urea, starch, calcium carbonate, kaolin, cyclodextrins, crystalline cellulose, silicic acid and the like; binders such as water, ethanol, propanol, simple syrup, glucose solutions, starch solutions, gelatin solutions, carboxymethyl cellulose, shelac, methyl cellulose, potassium phosphate, polyvinylpyrrolidone, etc. Additionally, disintegrating agents such as dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, etc., may be used. Disintegration inhibitors such as white sugar, stearin, coconut butter, hydrogenated oils; absorption accelerators such as quaternary ammonium base, sodium laurylsulfate, etc., may be used. Wetting agents such as glycerin, starch, and others known in the art may be used. Adsorbing agents such as, for example, starch, lactose, kaolin, bentonite, colloidal silicic acid, etc., may be used. Lubricants such as purified talc, stearates, boric acid powder, polyethylene glycol, etc., may be used. If tablets are desired, they may be further coated with the usual coating materials to make the tablets as sugar coated tablets, gelatin film coated tablets, tablets coated with enteric coatings, tablets coated with films, double layered tablets and multi-layered tablets. Pharmaceutical compositions adapted for topical administration may be formulated as ointments, creams, suspensions, lotions, powders, solutions, pastes, gels, foams, sprays, aerosols, or oils. Such pharmaceutical compositions may include conventional additives which include, but are not limited to, preservatives, solvents to assist drug penetration, co-solvents, emollients, propellants, viscosity modifying agents (gelling agents), surfactants and carriers.

The present approach may, in some embodiments, involve methods of testing compounds, and in particular mitoketoscins, for anti-cancer properties. As discussed above, vHTS and computational chemistry may be used to identify candidate mitochondrial inhibitors. Those candidates may be tested for specific anti-cancer properties. For example, the inventors compared seven candidate compounds in parallel for their ability to inhibit mammosphere formation in MCF7 cells. FIG. 3 demonstrates that six compounds tested inhibited mammosphere formation. Compound 2 and 8 (FIGS. 3A and 3B, respectively) were the two most potent candidates in decreasing the number of mammospheres, a measure of cancer stem cell activity, at a concentration of 25 µM. Compound 6 and 3 were also effective (FIGS. 3C and 3D, respectively), while compound 5 and 1 (FIGS. 3E and 3F, respectively) were less potent inhibitors of mammosphere growth.

TABLE 1

Mitoketoscin inhibition of mammosphere formation in MCF7 cells

| Compound | ID | IC-50 (µM) |
|---|---|---|
| OXCT1 Hits | | |
| 1 | ALB-H01004577 | 160.4 |
| 2 | ALB-H09465625 | 11.3 |
| 3 | ALB-H15358970 | 46.7 |
| 4 | ALB-H15354504 | 166.8 |

TABLE 1-continued

Mitoketoscin inhibition of mammosphere formation in MCF7 cells

| Compound | ID | IC-50 (µM) |
|---|---|---|
| ACAT1 Hits | | |
| 5 | ALB-H04367562 | 66.7 |
| 6 | LEG19576081 | 22.9 |
| 8 | ALB-H01005022 | 10.1 |

Table 1 summarizes the mammosphere formation inhibition results for seven candidate compounds. Table 1 shows that seven compounds inhibited mammosphere formation with half-maximal inhibitory concentrations (IC-50s) between 10 and 170 µM. Compounds 1 to 4 were identified from the OXCT1 screen, and Compounds 5, 6, and 8 were identified from the ACAT1 screen.

The present approach may, in some embodiments, involve methods of function validation of mitoketoscin compounds. For example, the inventors assessed functional validation of four candidates using the Seahorse Analyzer, which quantitatively measures oxygen consumption rate (OCR) and extracellular acidification rate (ECAR). OCR is a surrogate marker for OXPHOS and ECAR is a surrogate marker for glycolysis and L-lactate production.

Figure 4A:
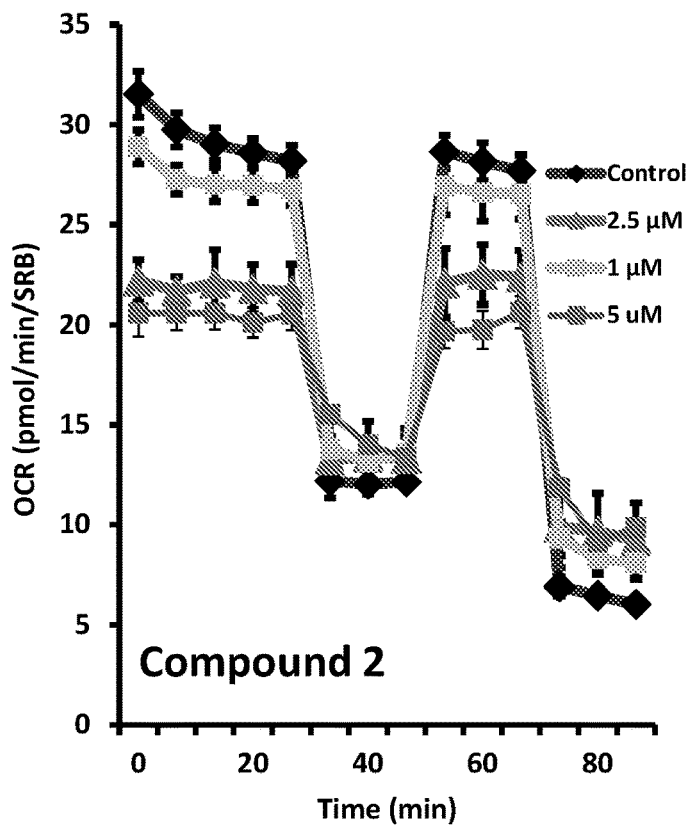
FIGS. 4A-D shows the effects of four candidate mitoketoscin compounds on ATP-depletion in MCF7 cells.
Figure 4B:
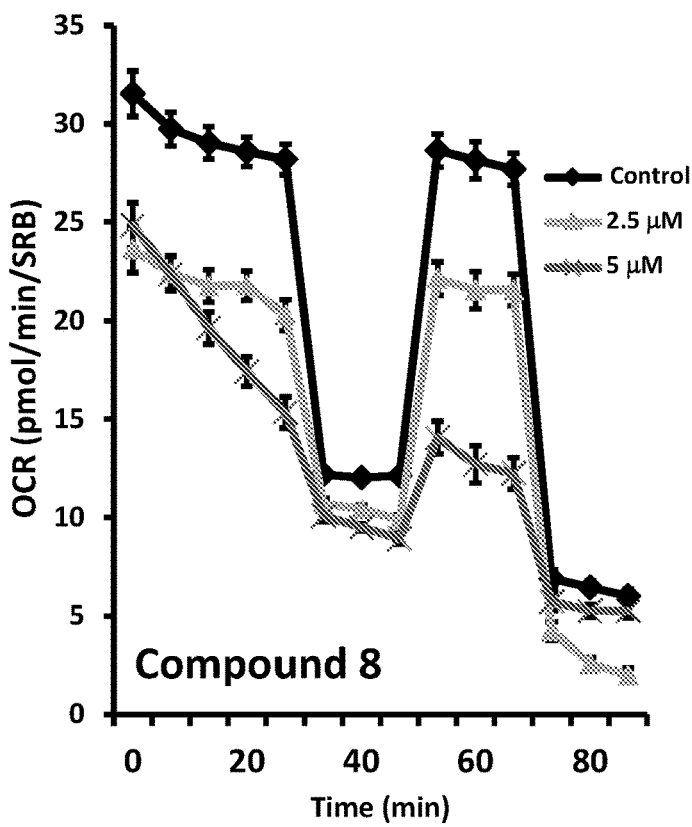
Figure 4C:
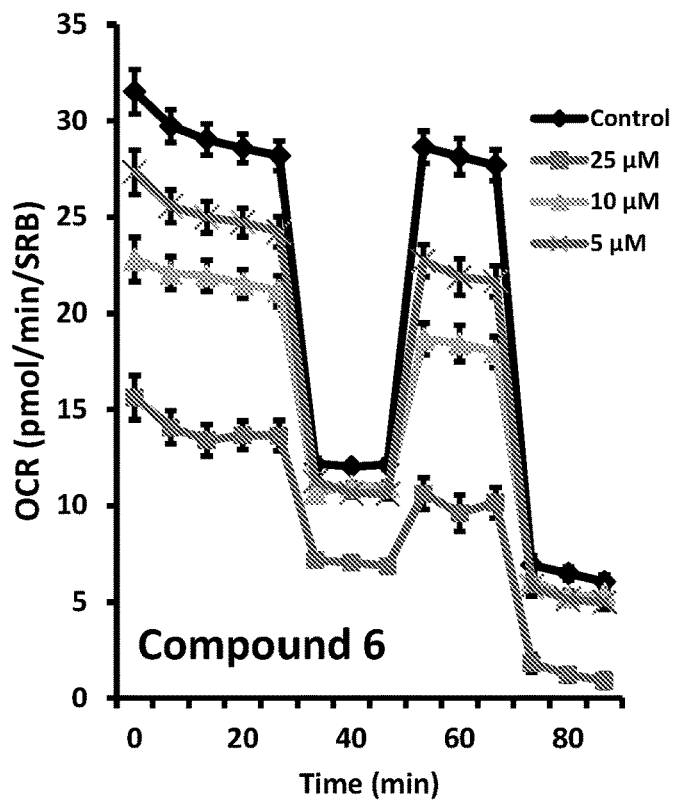
Figure 4D:
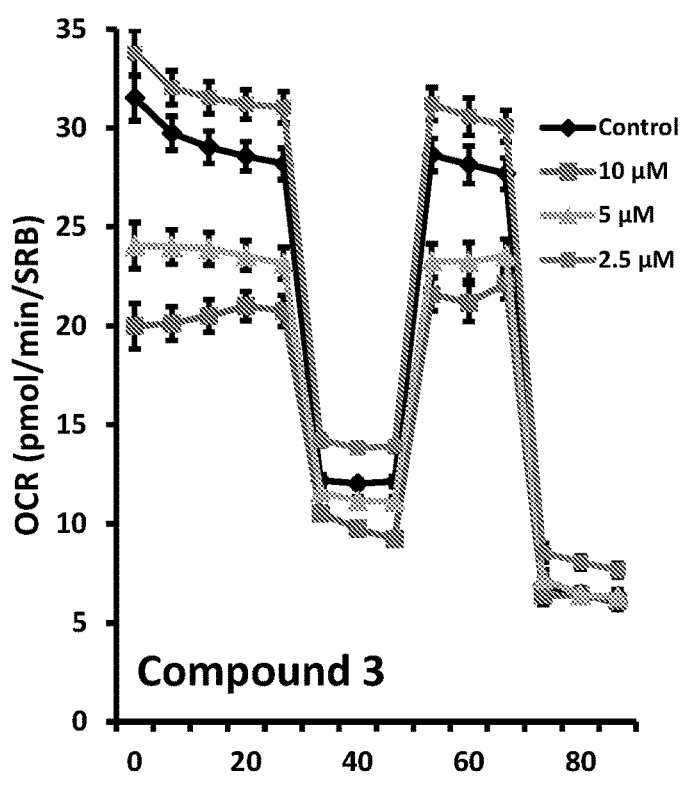
Figure 5A:
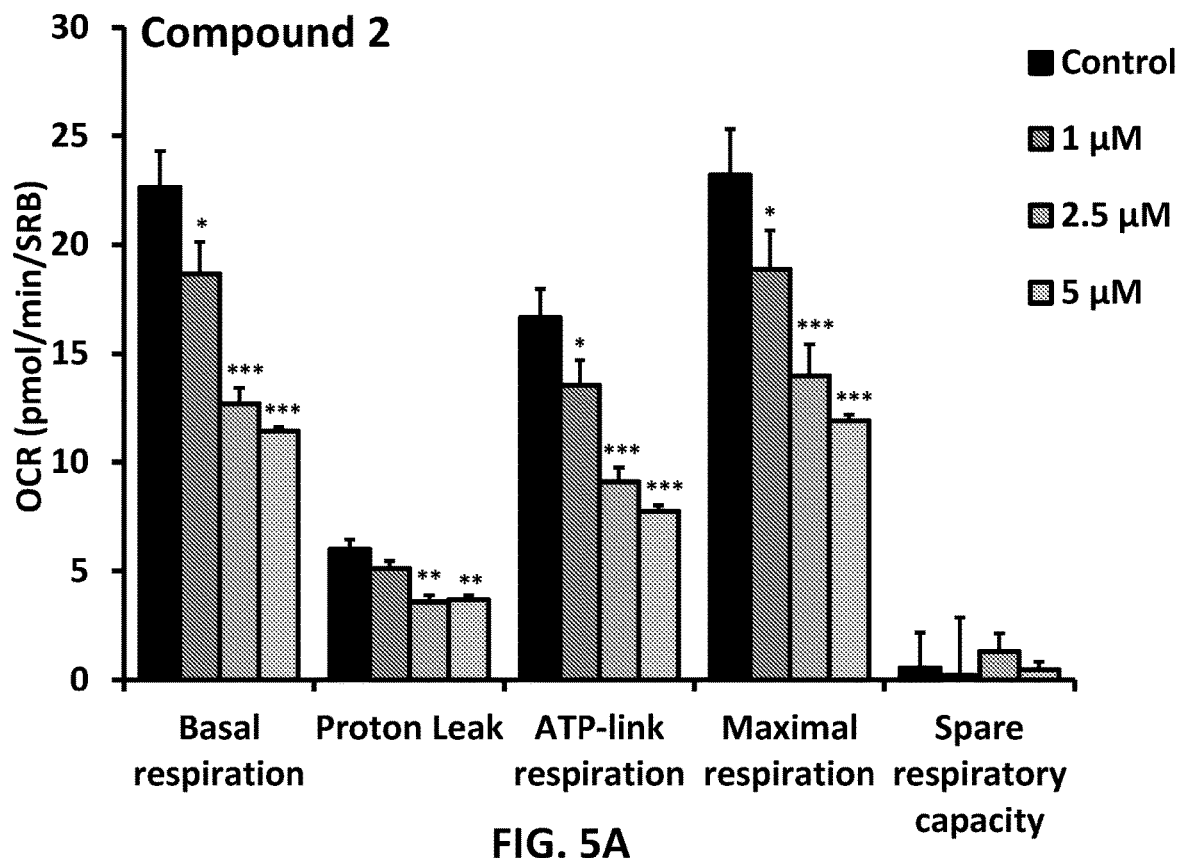
FIGS. 5A-B and 6A-B each show the effects of two candidate mitoketoscin compounds on basal respiration, proton leak, ATP-linked respiration, maximal respiration, and spare respiratory capacity in MCF7 cells.
Figure 5B:
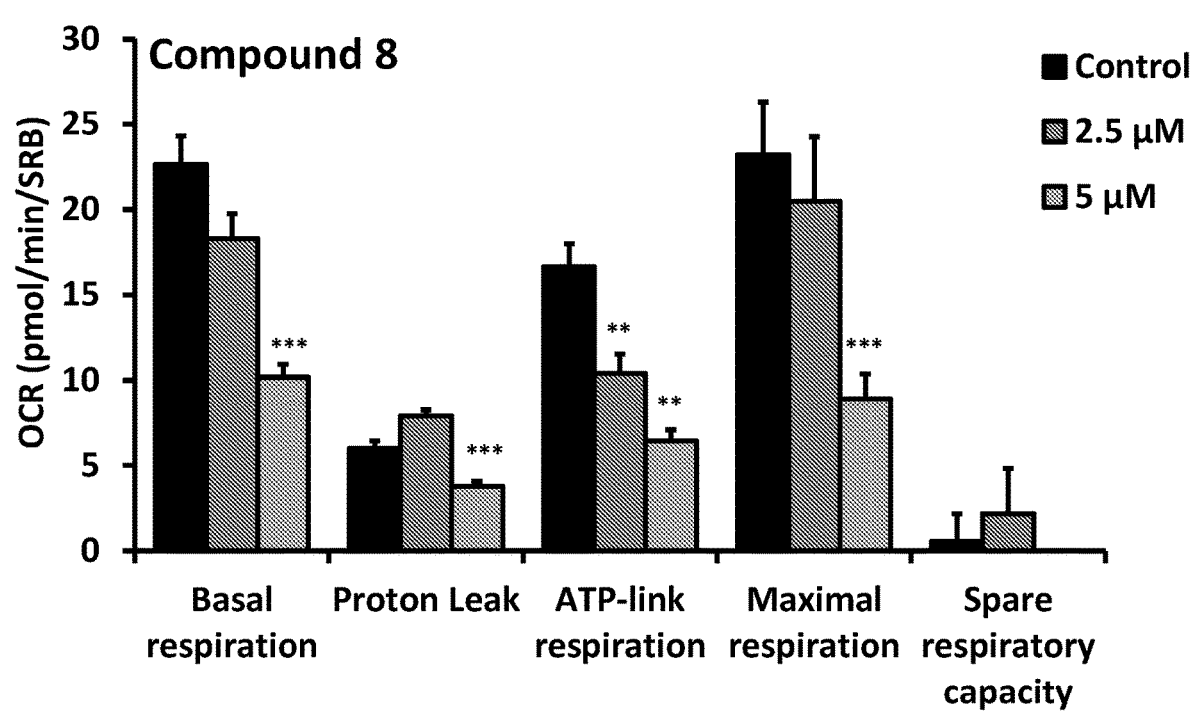
Figure 6A:
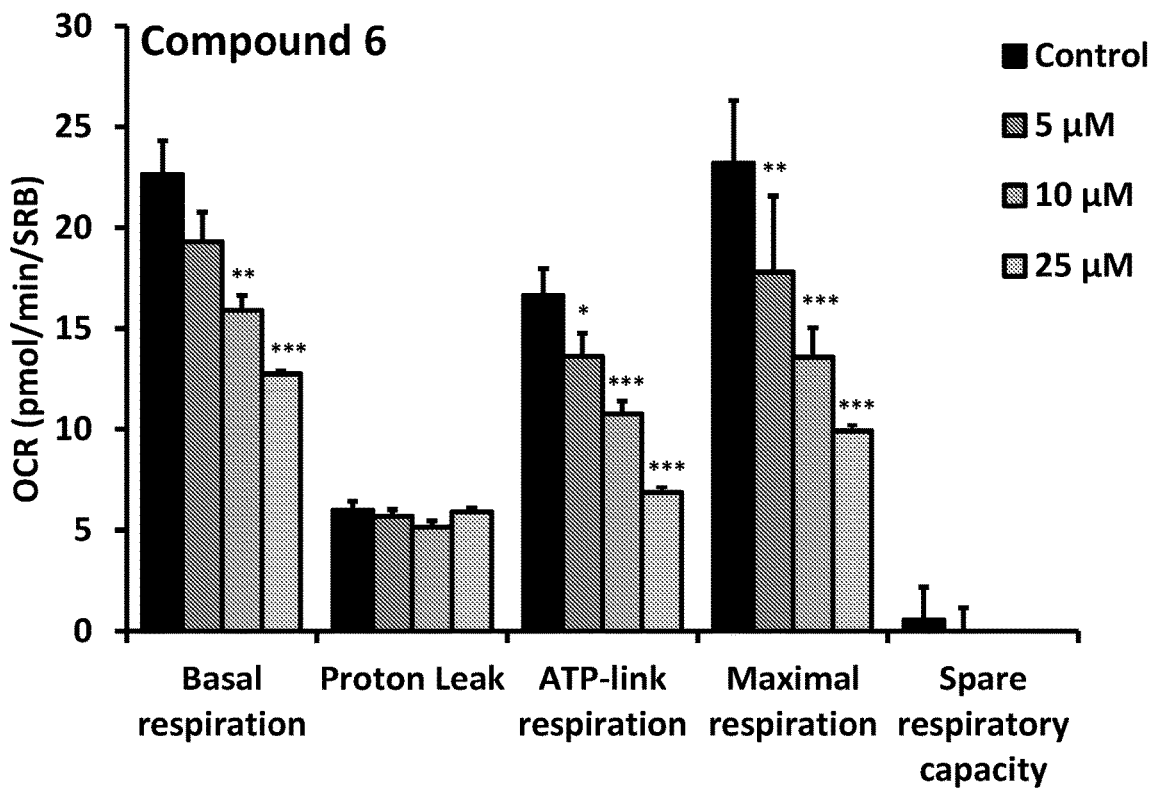
Figure 6B:
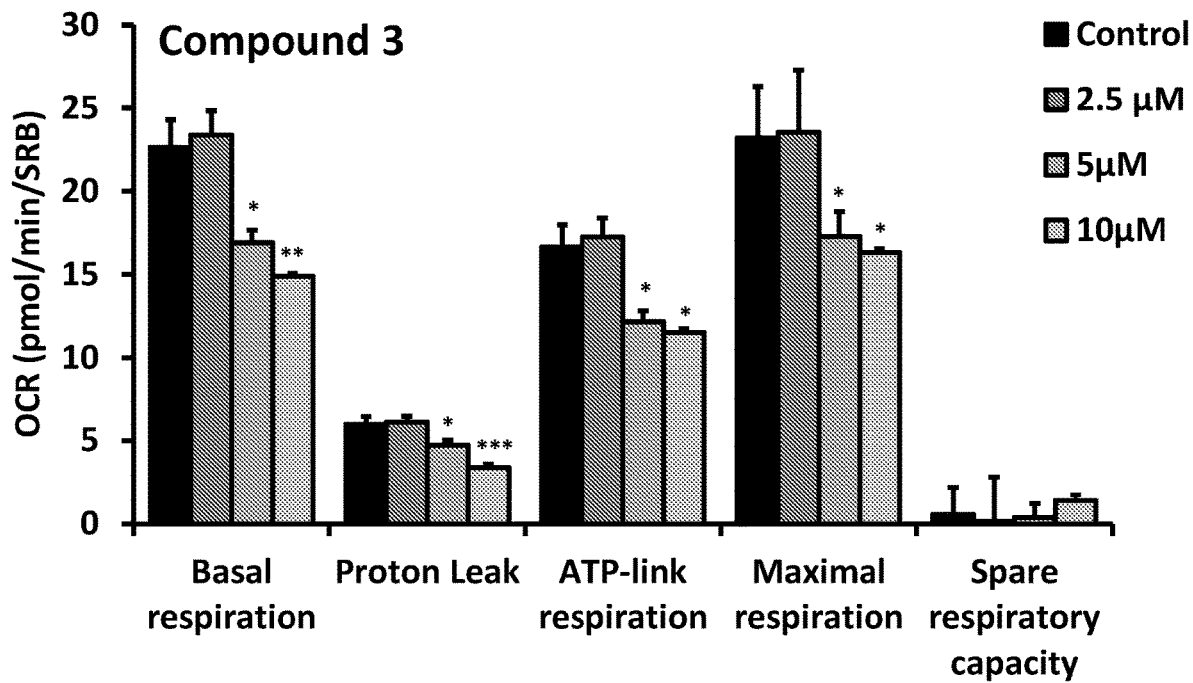
Figure 7A:
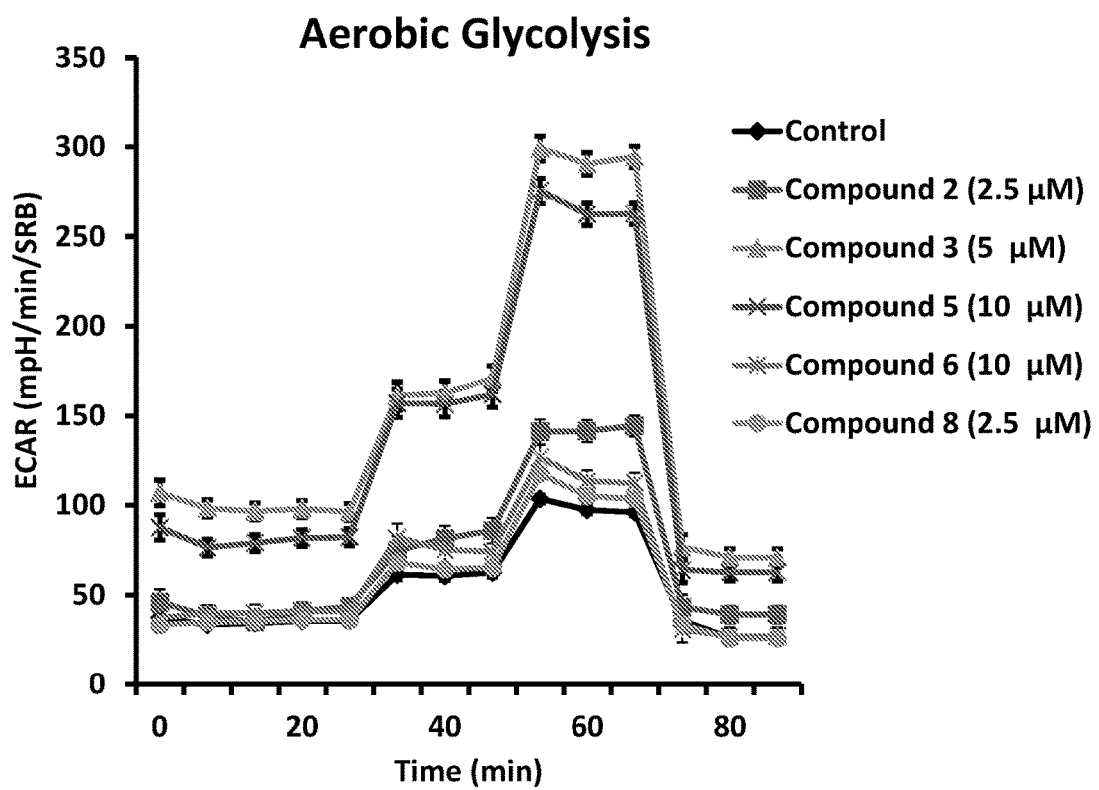
FIG. 7A shows the effects of five candidate mitoketoscin compounds on aerobic glycolysis in MCF7 cells.
Figure 7B:
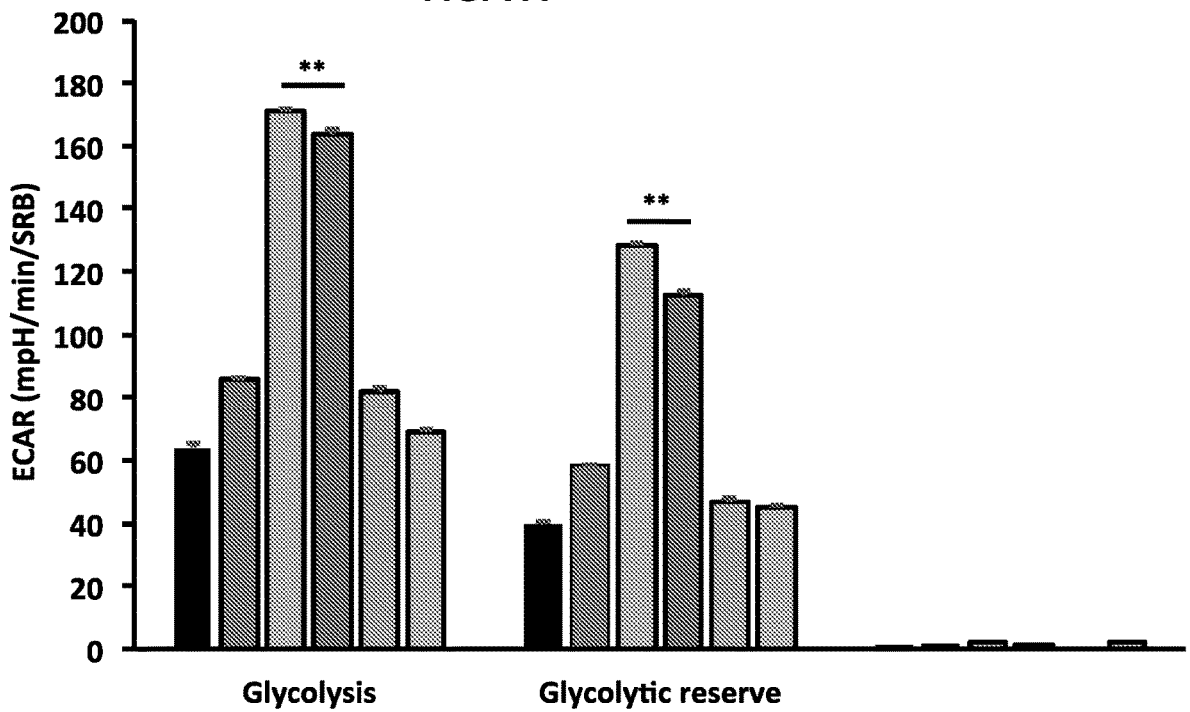
FIG. 7B shows the effects of five candidate mitoketoscin compounds on extracellular acidification rate (ECAR) over time in MCF7 cells.

The inventors' results demonstrated that Compounds 2, 3, 6, and 8 all dose-dependently inhibited mitochondrial oxygen-consumption in MCF7 cells. FIGS. 4A and 4B show that Compounds 2 and 8 reduced mitochondrial respiration significantly, even at doses as low as 5 µM. Compounds 6 and 3 were also potent inhibitors (FIGS. 4C and 4D). As shown in FIGS. 5 and 6, the compounds dosed dependently reduced basal respiration, proton leak, ATP-linked respiration, and maximal respiration. FIG. 7 shows how four compounds significantly inhibited glycolysis compared to the control.

Some embodiments of the present approach may include testing compounds for anti-cancer properties by considering compound effects on mammosphere formation. It should be appreciated that those skilled in the art may use other methods known in the art for assessing a candidate mitochondrial inhibitor's effects on a particular cell line without departing from the present approach. It should also be appreciated that those skilled in the art may assess a candidate mitochondrial inhibitor's effects on other cancer types, as the inhibitors target cancer stem cells (CSCs). CSCs show conserved or similar features across most cancer types.

Figure 8A:
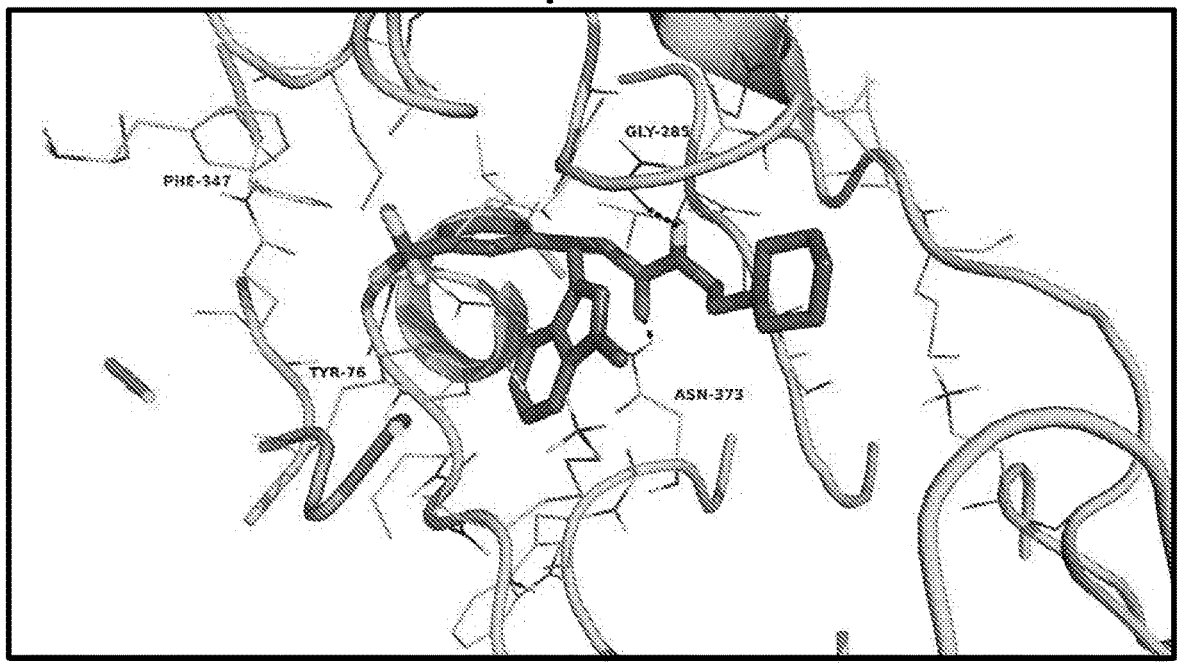
FIGS. 8A-D illustrate docking images of four candidate mitoketoscin compounds.
Figure 8B:
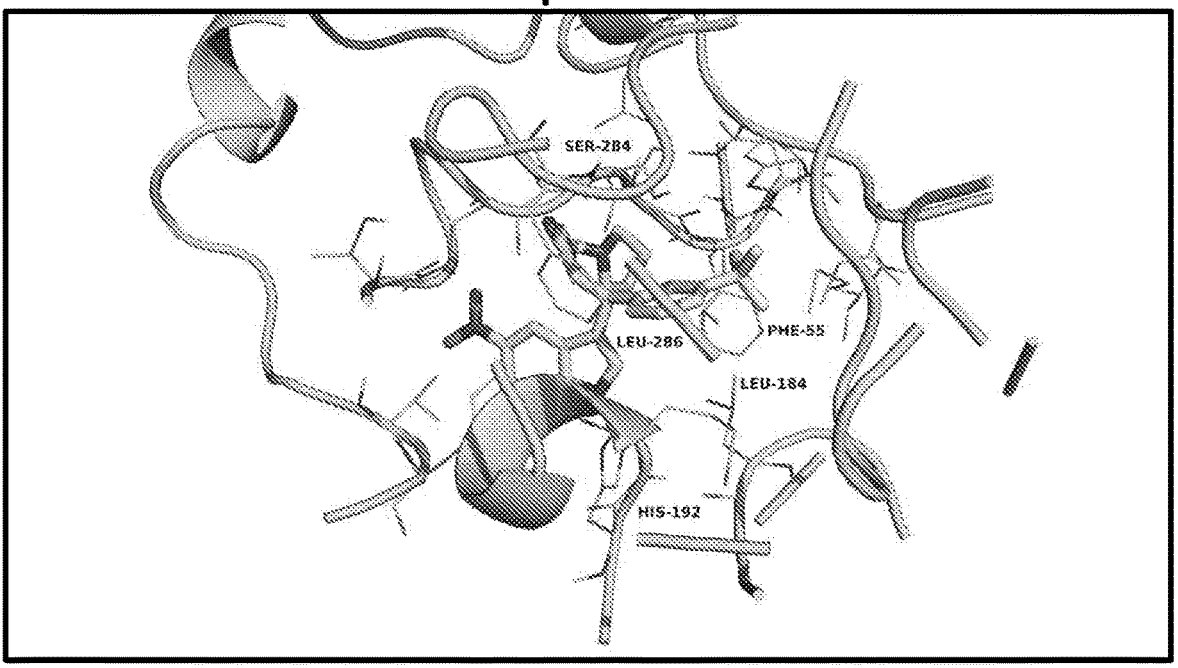
Figure 8C:
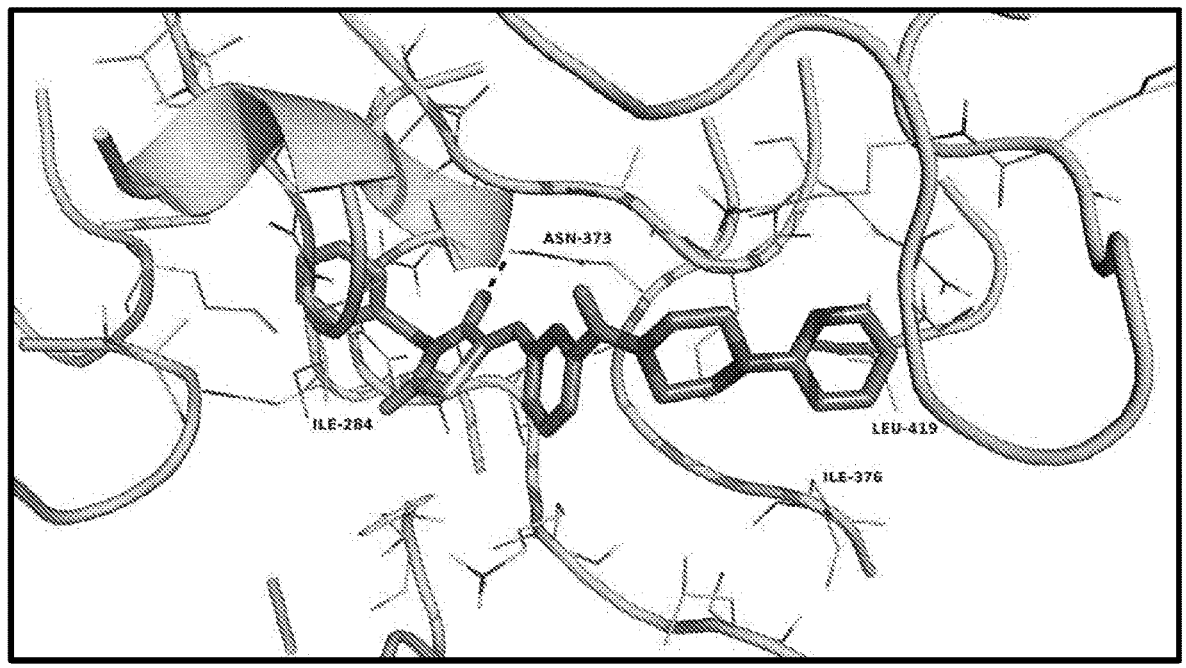
Figure 8D:
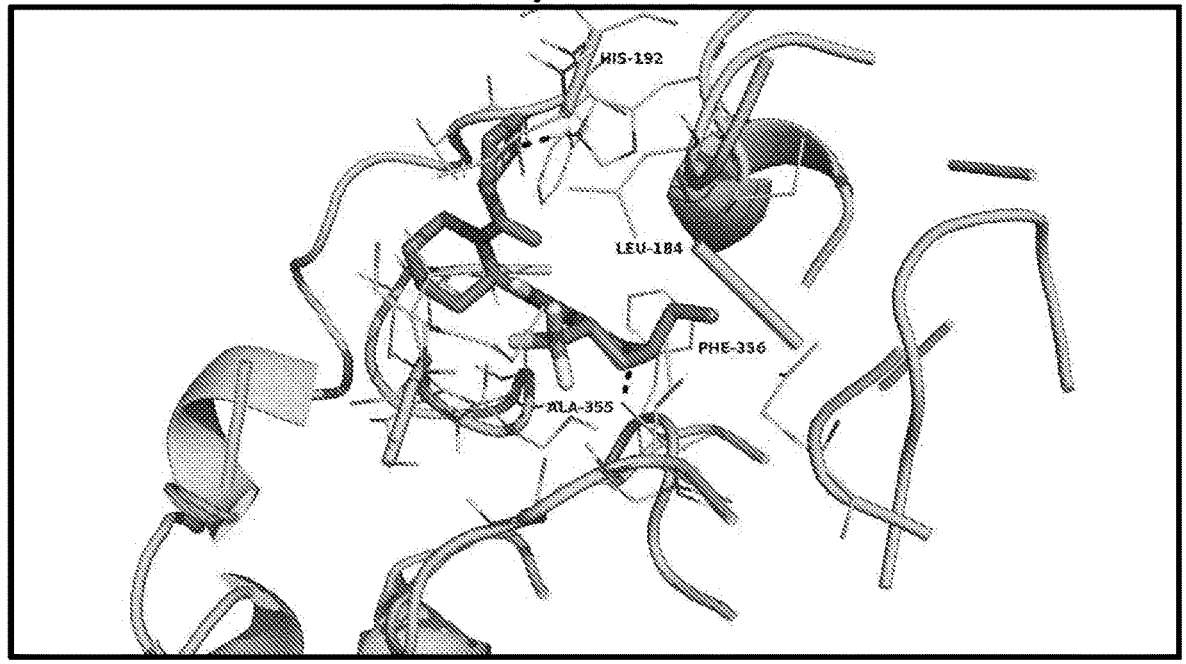

FIGS. 8A-8D illustrate the molecular modeling of Compounds 2, 8, 3, and 6. The goal of molecular modeling is to predict the predominant binding mode of a compound to a known three dimensional structure. FIG. 8A and 8C show the molecular docking of Compounds 2 and 3, respectively, at the succinyl-CoA binding site within the 3D crystal structure of OXCT1. A comparison of FIG. 8A and 8C shows that at least one amino acid, ASN-373, is predicted to directly bind to both Compounds 2 and 3. FIGS. 8B and 8D shows the molecular docking of Compounds 8 and 6, respectively, at the CoA binding site within the 3D crystal structure of ACAT1. A comparison of FIG. 8B and 8D shows that at least two amino acids, LEU-184 and HIS-192, are predicted to directly bind to both Compounds 8 and 6. These predicted dominant binding modes may be invaluable to further lead optimization.

Figure 9:
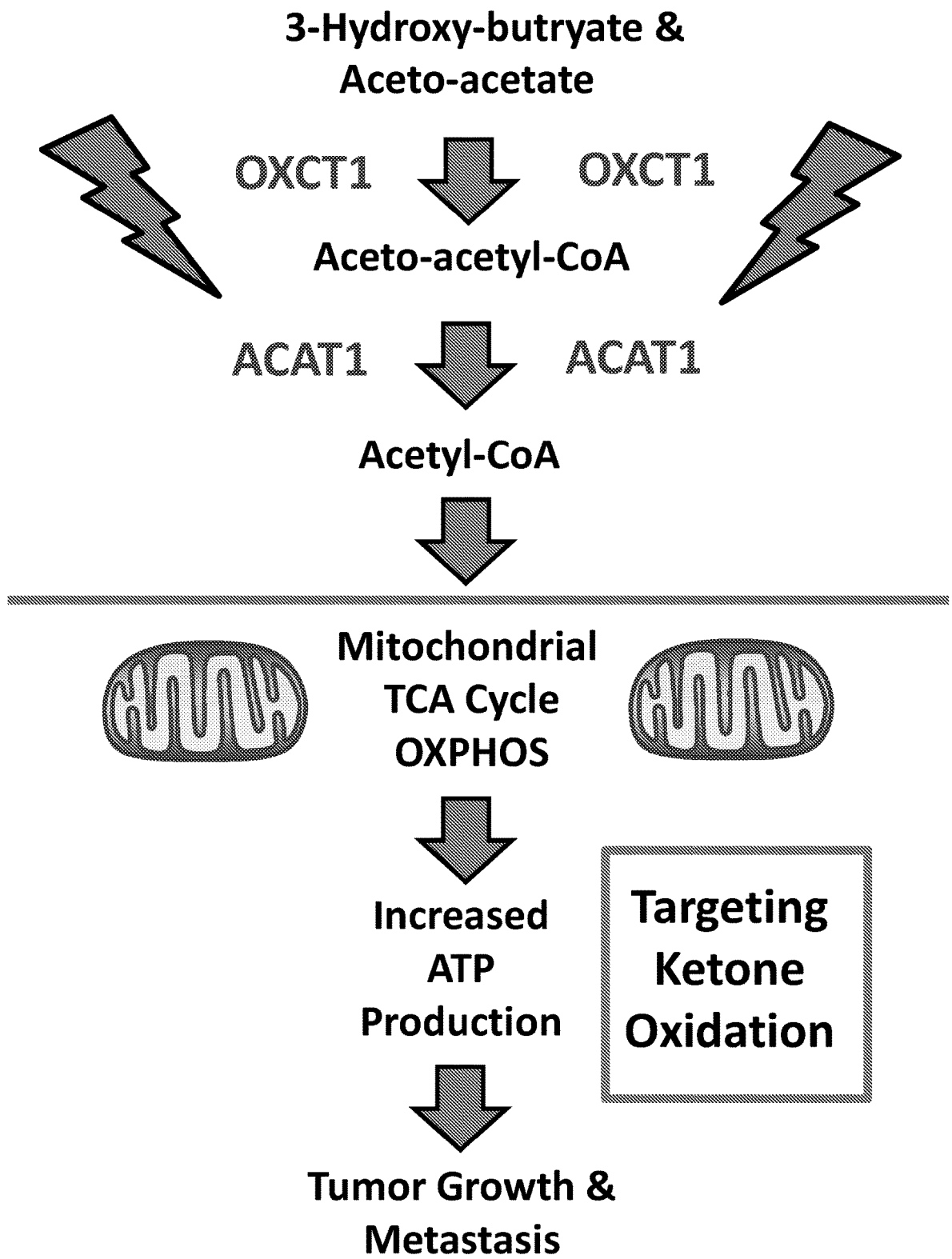
FIG. 9 shows a schematic diagram outlining how OXCT1 and ACAT1 function to drive ATP production.

Ketone bodies functionally behave as mitochondrial fuels, which may actively drive tumor growth and metastasis. In this context, OXCT1 and ACAT1 are two mitochondrial proteins that participate in ketone re-utilization, as is summarized in FIG. 9. The inventors molecularly targeted OXCT1 and ACAT1 to prevent cancer cells from recycling ketone bodies into Acetyl-CoA, which normally enters the TCA cycle, driving mitochondrial ATP production.

Figure 11B:
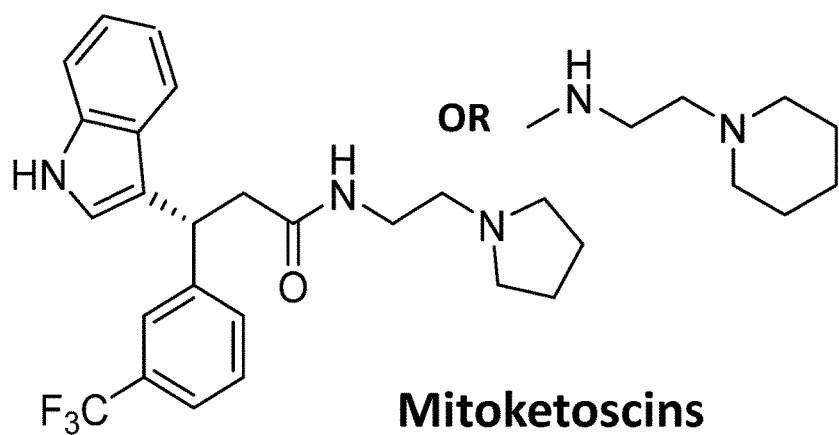
FIG. 11B shows the pharmacophores for two candidate mitoketoscin compounds.
Figure 12A:
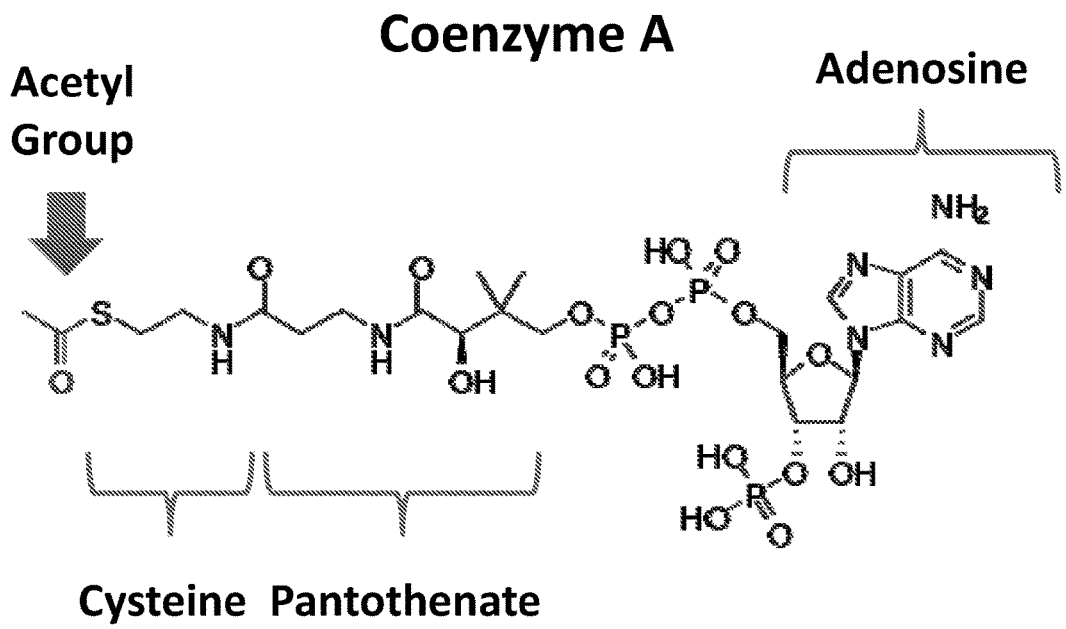
FIG. 12A shows the structure of Coenzyme A (CoA).
Figure 12B:
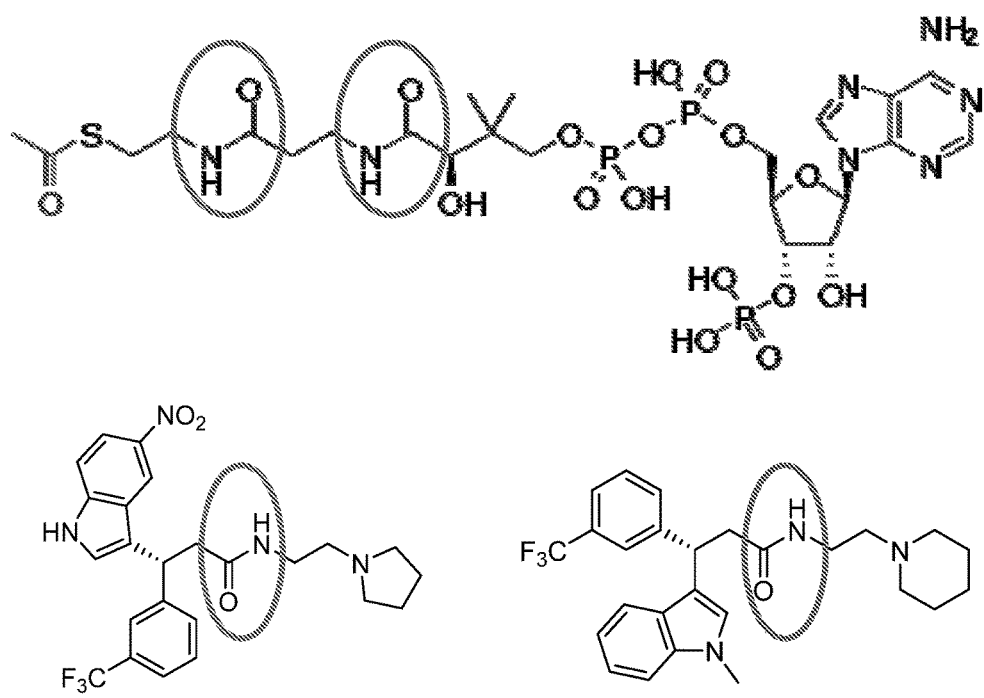
FIG. 12B compares the structure of CoA with two candidate mitoketoscin compounds.

A top hit for the OXCT1 screen (Compound 2) and a hit for the ACAT1 screen (Compound 8) have similar chemical structures, with the exception of minor functional side groups, as shown in FIG. 10A. The underlying "chemical scaffold" or pharmacophore is the same for both small molecules, as shown in FIG. 11B. The structures of Compounds 2 and 8 were also compared to the molecular structure of Coenzyme A in FIG. 12 to demonstrate structural similarities.

Figure 11A:
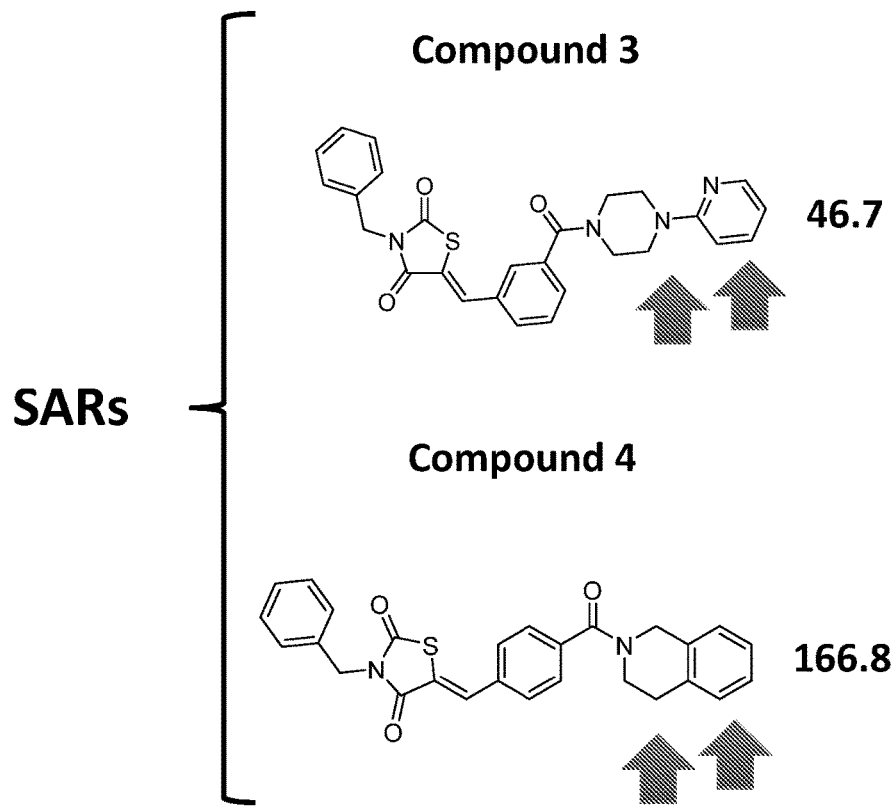
FIG. 11A compares the structures of two candidate mitoketoscin compounds.

Two compounds from the OXCT1 screen (Compounds 3 and 4) are structurally similar to each other, as is shown in FIG. 11A. However, based on their observed IC-50 values, Compound 3 is nearly 4 times more potent than Compound 4 in its ability to target CSC propagation. The unique chemical groups that distinguish these two molecules structurally (highlighted by arrows in FIG. 11A), may be responsible for the observed differences in their IC-50s observed for their inhibition of CSC propagation.

Recent studies provide additional evidence of a role for ACAT1 as an oncogene, as these studies identified arecoline as a potential ACAT1 inhibitor. Garcia-Bermudez et al, *Mol Cell* 2016, 64(5):856-857. Arecoline is a nicotinic acid-based alkaloid found within the areca nut, which is the fruit of the areca palm tree (Areca catechu). Arecoline has shown anti-tumor activity, further validating that drugs targeting ACAT1 might be valuable as anti-cancer agents. However, the inventors did not assess its capacity to target CSCs. As arecoline is very small molecule (shown in FIG. 10B for comparison to Compounds 6 and 3), it may need to be modified significantly by medicinal chemistry to increase its potency. Arecoline is not a mitoketoscin, because the compound is known to be carcinogenic.

Figure 13:
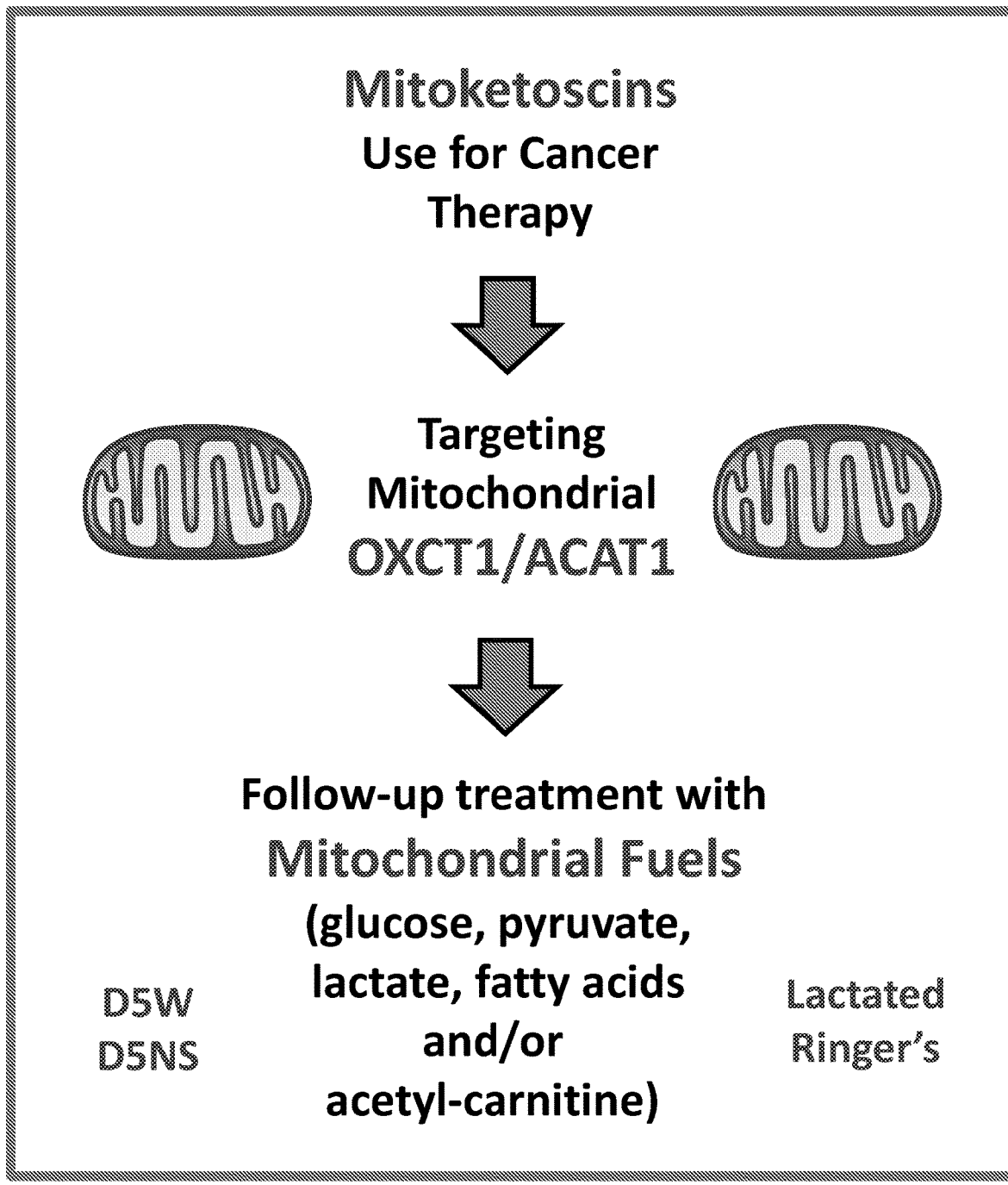
FIG. 13 shows a schematic diagram outlining a follow-up treatment strategy with mitochondrial substrates to ameliorate potential side effects of mitoketoscins, according to embodiments of the present approach.

While normal ketone metabolism occurs under conditions of organismal starvation and/or severe nutrient deprivation, this regulation is lost in human tumors, and ketone metabolism appears to occur constitutively in cancer cells. Targeting ketone metabolism in human tumors, under normal dietary conditions, would be predicted to have minimal metabolic side effects. Nevertheless, the potential side-effects of ketone inhibitors could be significantly ameliorated or "controlled" by including a "rescue" step, consisting of a follow-up treatment with other mitochondrial support substrates, such as glucose, pyruvate, lactate, fatty acids and/or acetyl-carnitine, as is shown in FIG. 13. Sterile D-glucose and L-lactate intravenous solutions (D5W, D5NS, Lactated Ringer's) are already used routinely in hospitals for other clinical and therapeutic indications; hence, a follow-up treatment is clinically feasible.

The inventors have shown that compounds inducing acute ATP depletion in cancer cells may sensitize those cells to radiation, ultraviolet light, chemotherapeutic agents, natural substances, and/or caloric restriction. Mitoketoscins, as discussed herein, have demonstrated ATP-depletion effects. Based on these preliminary results, mitoketoscins may also be used as radiosensitizers and/or photo-sensitizers. Use as radiosensitizers and/or photo-sensitizers may be in combination with other treatment vectors, including but not limited to other cancer treatment methods as may be known in the art, and cancer treatment through inhibiting mitochondrial biogenesis as disclosed herein. Similarly, mitoketoscins may be used to functionally sensitize bulk cancer cells and cancer stem cells to chemotherapeutic agents, pharmaceuticals, and/or other natural substances, such as dietary supplements and caloric restriction.

In addition to anti-cancer and anti-biotic behavior, the mitochondrial inhibitors that may be identified by the present approach have the potential to slow the mammalian aging process. Genetic inhibition of mitochondrial protein translation has been shown to have beneficial side-effects, and in particular the side effect of slowing the aging process and increasing lifespan in model organisms. Lower steady-state levels of Mrps5 (a mitoribosomal protein) are strongly functionally correlated with longer murine lifespan, resulting in a significant lifespan increase of ~250 days. In addition, selective knock-down of Mrps5 in *C. elegans* dramatically increases lifespan. Mrps5 knock-down worms show significant decreases in mitochondrial respiration and ATP production. Similarly, knock-down of the worm homologs of mitochondrial complex I, III, IV and V, as well as several TCA cycle enzymes, all robustly extended lifespan, further implicating reduced OXPHOS activity and lower ATP levels as the mechanism. Finally, pharmacological inhibition of mitochondrial biogenesis (using the off-target effects of doxycycline) also significantly increases lifespan in *C. elegans*. Thus, mitoketoscins may be used to therapeutically target the aging process and to extend lifespan.

Mitoketoscins may also be used to minimize and/or reverse drug resistance in cancer cells. Drug resistance is thought to be based, at least in part, on increased mitochondrial function in cancer cells. In particular, cancer cells demonstrating resistance to endocrine therapies, such as tamoxifen, are expected to have increased mitochondrial function. Mitoketoscins inhibit mitochondrial function, and therefore may be useful in reducing and, in some cases reversing, drug resistance in cancer cells.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed a element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measureable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A pharmaceutical composition comprising, as an active ingredient, a compound having the general formula:

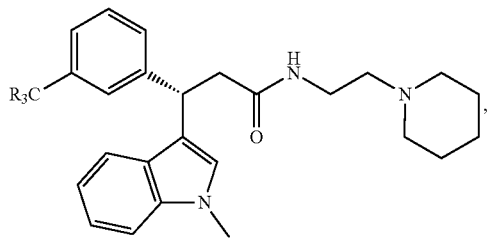

wherein each R may be the same or different and is selected from the group consisting of hydrogen, fluorine, chlorine, bromine, iodine, carboxyl, alkanes, cyclic alkanes, alkenes, cyclic alkenes, alkynes, ketones, aldehydes, carboxylic acids, ethers, esters, amines, amides, monocyclic or polycyclic arene, heteroarenes, phenols, and benzoic acid; and
a pharmaceutically acceptable carrier or excipient;
wherein the concentration of the active ingredient is sufficient to inhibit the formation of MCF7 mammospheres in a human tumor; and
wherein the pharmaceutical composition is in a form selected from the group comprising a tablet, a pill, a powder, and a capsule.

2. The pharmaceutical composition of claim 1, wherein each R is fluorine.

3. The pharmaceutical composition of claim 1, wherein the pharmaceutically acceptable carrier or excipient comprises at least one of lactose, white sugar, sodium chloride, glucose, urea, starch, calcium carbonate, kaolin, cyclodextrin, crystalline cellulose, and silicic acid.

4. The pharmaceutical composition of claim 1, wherein the pharmaceutically acceptable carrier or excipient comprises at least one of water, ethanol, propanol, simple syrup, a glucose solution, a starch solution, a gelatin solution, carboxymethyl cellulose, shelac, methyl cellulose, potassium phosphate, and polyvinylpyrrolidone.

5. The pharmaceutical composition of claim 1, wherein the pharmaceutically acceptable carrier or excipient comprises at least one of sodium alginate, agar powder, laminalia powder, sodium hydrogen carbonate, calcium carbonate, fatty acid esters of polyoxyethylene sorbitan, sodium laurylsulfate, a monoglyceride of stearic acid, and lactose.

6. A pharmaceutical composition comprising, as an active ingredient, a compound having the general formula:

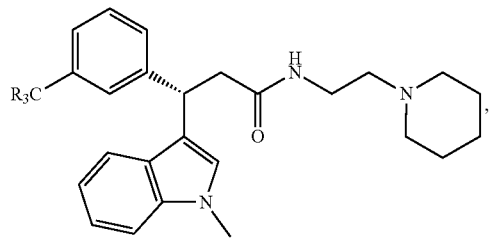

wherein each R may be the same or different and is selected from the group consisting of hydrogen, fluorine, chlorine, bromine, iodine, carboxyl, alkanes, cyclic alkanes, alkenes, cyclic alkenes, alkynes, ketones, aldehydes, carboxylic acids, ethers, esters, amines, amides, monocyclic or polycyclic arene, heteroarenes, phenols, and benzoic acid; and
a pharmaceutically acceptable carrier or excipient;
wherein the concentration of the active ingredient is sufficient to inhibit the formation of MCF7 mammospheres in a human tumor; and
wherein the pharmaceutically acceptable carrier or excipient comprises at least one of lactose, white sugar, glucose, urea, starch, kaolin, cyclodextrin, crystalline cellulose, silicic acid, ethanol, propanol, simple syrup, a glucose solution, a starch solution, a gelatin solution, carboxymethyl cellulose, shelac, methyl cellulose, potassium phosphate, polyvinylpyrrolidone, sodium alginate, agar powder, laminalia powder, sodium hydrogen carbonate, calcium carbonate, fatty acid esters of polyoxyethylene sorbitan, sodium laurylsulfate, a monoglyceride of stearic acid, and lactose.

7. The pharmaceutical composition of claim 6, wherein the pharmaceutical composition is in a form selected from the group consisting of a tablet, a pill, a powder, a capsule, a suspension, and an emulsion.

* * * * *